(12) United States Patent
Kanick et al.

(10) Patent No.: US 11,751,767 B2
(45) Date of Patent: Sep. 12, 2023

(54) STRUCTURED-LIGHT IMAGING SYSTEMS AND METHODS FOR DETERMINING SUB-DIFFUSE SCATTERING PARAMETERS

(71) Applicant: The Trustees of Dartmouth College, Hanover, NH (US)

(72) Inventors: Stephen Chad Kanick, Lebanon, NH (US); Brian William Pogue, Hanover, NH (US); Keith D. Paulsen, Hanover, NH (US); Jonathan T. Elliott, West Lebanon, NH (US); David M. McClatchy, III, Hanover, NH (US); Venkataramanan Krishnaswamy, Lebanon, NH (US)

(73) Assignee: The Trustees of Dartmouth College, Hanover, NH (US)

( * ) Notice: Subject to any disclaimer, the term of this patent is extended or adjusted under 35 U.S.C. 154(b) by 542 days.

(21) Appl. No.: 16/673,165

(22) Filed: Nov. 4, 2019

(65) Prior Publication Data

US 2020/0069187 A1 Mar. 5, 2020

Related U.S. Application Data

(63) Continuation of application No. 15/013,623, filed on Feb. 2, 2016, now Pat. No. 10,463,256, which is a
(Continued)

(51) Int. Cl.
*A61B 5/00* (2006.01)
(52) U.S. Cl.
CPC ........ *A61B 5/0075* (2013.01); *A61B 2576/00* (2013.01)

(58) Field of Classification Search
CPC .............. A61N 5/062; A61N 2005/063; A61N 2005/0662; A61N 2005/067; F21K 9/64;
(Continued)

(56) References Cited

U.S. PATENT DOCUMENTS

| 4,523,809 A | 6/1985 | Taboada et al. |
| 7,729,750 B2 | 6/2010 | Tromberg et al. |

(Continued)

FOREIGN PATENT DOCUMENTS

WO 2014043609 3/2014

OTHER PUBLICATIONS

Bevilacqua et al. (1999) "Monte Carlo study of diffuse reflectance at source-detector separations close to one transport mean free path," J. Opt. Soc. Am. A. 16(12): 2935-2945.
(Continued)

*Primary Examiner* — Deborah L Malamud
(74) *Attorney, Agent, or Firm* — Cozen O'Connor

(57) ABSTRACT

A method for determining sub-diffuse scattering parameters of a material includes illuminating the material with structured light and imaging remission by the material of the structured light. The method further includes determining, from captured remission images, sub-diffuse scattering parameters of the material. A structured-light imaging system for determining sub-diffuse scattering parameters of a material includes a structured-light illuminator, for illuminating the material with structured light of periodic spatial structure, and a camera for capturing images of the remission of the structured light by the material. The structured-light imaging system further includes an analysis module for processing the images to quantitatively determine the sub-diffuse scattering parameters. A software product includes machine-readable instructions for analyzing images of remission of structured light by a material to determine sub-diffuse scattering parameters of the material.

15 Claims, 16 Drawing Sheets

Related U.S. Application Data continuation-in-part of application No. PCT/US2015/014416, filed on Feb. 4, 2015.

(60) Provisional application No. 62/110,882, filed on Feb. 2, 2015, provisional application No. 61/935,803, filed on Feb. 4, 2014.

(58) Field of Classification Search
CPC ............ G02B 21/0056; G02B 21/008; G02B 23/2453; G02B 23/26; G02B 27/283; G02B 5/003; G02B 5/0242; G02B 5/0278; G06T 7/0012; G06T 7/586; A61B 5/0075; A61B 5/0017; A61B 5/0095
See application file for complete search history.

(56) References Cited

U.S. PATENT DOCUMENTS

| | | | |
|---|---|---|---|
| 2006/0184043 A1 | 8/2006 | Tromberg et al. | |
| 2009/0036902 A1 | 2/2009 | Dimaio et al. | |
| 2011/0124988 A1* | 5/2011 | Cuccia .............. | A61B 5/0059 600/310 |
| 2013/0044185 A1 | 2/2013 | Krishnaswamy et al. | |

OTHER PUBLICATIONS

Calabro et al. (Feb. 9, 2012) "Improved empirical models for extraction of tissue optical properties from reflectance spectra," Proc. SPIE. 8230:82300H. pp. 1-7.

Cuccia et al. (2005) "Modulated imaging: quantitative analysis and tomography of turbid media in the spatial-frequency domain," Opt. Lett. 30(11):1354-1356.

Cuccia et al. (2009) "Quantitation and mapping of tissue optical properties using modulated imaging," J Biomed. Op. 14(2):024012. pp. 1-13.

Gamm (Oct. 4, 2013) Quantification of Tissue Scattering Properties by Use of Fiber Optic Spectroscopy, Uitgeverij BOXPress,'s-Hertogenbosch, 138 pgs.

Gioux et al. (2009) "Three-dimensional surface profile intensity correction for spatially modulated imaging," J. Biomed Opt. 14:034045. pp. 1-11.

Gioux et al. (2011) "First-in-human pilot study of spatial frequency domain oxygenation imaging system," J. Biomed. Opt. 16(8):086015. pp. 1-10.

Jacques et al. (2008) "Tutorial on diffuse light transport," J. Biomed. Opt. 13(4):041302. pp. 1-19.

Johnson et al. (2000) "Optical light scatter imaging of cellular and sub-cellular morphology changes in stressed rat hippocampal slices," J. Neurosci. Methods. 98:21-31.

Kanick et al. (May 1, 2012) "Scattering phase function spectrum makes reflectance spectrum measured from ntralipid phantoms and tissue sensitive to the device detection geometry," Biomed. Opt. Express. 3(5):1086-1100.

Kanick et al. (May 20, 2011) "Method to quantitatively estimate wavelength-dependent scattering properties from multidiameter single fiber reflectance spectra measured in a turbid medium," Optics Letters 36(15): 2997-2999.

Kanick et al. (Sep. 3, 2014) "Sub-diffusive scattering parameter maps recovered using wide-field high-frequency structured light imaging," Biomedical Optics Express. 5(10):3376-3390.

Konecky et al. (2011) "Imaging scattering orientation with spatial frequency domain imaging," J. Biomed. Opt. 16 (12):126001. pp. 1-8.

Krishnaswamy et al. (Nov. 6, 2014) "Structured light scatteroscopy," Journal of Biomedical Optics. 19 (7):070504. pp. 1-1.

Krishnaswamy et al. (2011) "Dark-field scanning in situ spectroscopy platform for broadband imaging of resected tissue," Opt. Lett. 36:1911-1913.

Krishnaswamy et al. (2009) "Quantitative imaging of scattering changes associated with epithelial proliferation, necrosis, and fibrosis in tumors using microsampling reflectance spectroscopy," J. Biomed. Opt. 14(1):014004. pp. 1-10.

Laughney et al. (2008) "System analysis of spatial frequency domain imaging for quantitative mapping of surgically resected breast tissue," J. Biomed. Opt. 18(3):036012. pp. 1-11.

Laughney et al. (Aug. 20, 2012) "Scatter spectroscopic imaging distinguishes between breast pathologies in tissues relevant to surgical margin assessment," Clin. Cancer Res 18(22):6315-6325.

Neil et al. (1997) "Method of obtaining optical sectioning by using structured light in a conventional microscope," Optical Society of America. 22(24):1905-1907.

Qian et al. (2010) "Dark-field light scattering imaging of living cancer cell component from birth through division using bioconjugated gold nanoprobes," J. Biomed. Opt 15:046025. pp. 1-9.

International Search Report with Written Opinion corresponding to International Patent Application No. PCT/US2015/014416, dated May 14, 2015.

\* cited by examiner

STRUCTURED-LIGHT IMAGING SYSTEMS AND METHODS FOR DETERMINING SUB-DIFFUSE SCATTERING PARAMETERS

CROSS-REFERENCES TO RELATED APPLICATIONS

The present application is a continuation of U.S. patent application Ser. No. 15/013,623, filed Feb. 2, 2016, which is a continuation in part of PCT Patent Application Serial No. PCT/US2015/014416 filed on Feb. 4, 2015, which claims priority to U.S. Provisional Patent Application Ser. No. 61/935,803 filed on Feb. 4, 2014. U.S. patent application Ser. No. 15/013,623 further claims priority to U.S. Provisional Patent Application Ser. No. 62/110,882, filed on Feb. 2, 2015. All of the aforementioned applications are incorporated herein by reference in their entireties.

U.S. GOVERNMENT RIGHTS

This invention was made with government support under grant number CA164248 awarded by the National Institutes of Health. The government has certain rights in the invention.

BACKGROUND

Light scattering in biological tissue is a complex process that occurs as photons traverse index of refraction mismatches along their propagation path. The index mismatches are associated with tissue morphology (e.g. cytoskeletal arrangement) and cellular ultrastructure (e.g. size and shape of nucleus, mitochondria, other cytoplasmic organelles). Measurements of scattering remission spectra have shown sensitivity to sub-cellular morphological changes in biological tissue; these observations support the use of scattering as an endogenous and label-free contrast mechanism to differentiate between tissue types. Scattering spectroscopy has important clinical implications for the diagnosis of cancers, and for the assessment of surgical margins to guide tumor resections.

While scatter remission spectra are sensitive to biological structure and morphology, the biological information that is encoded in collected spectra is dependent on the light transport regime that is sampled. Scattering interactions between photons and tissue can be described by a basic set of parameters including (a) the frequency of scattering events characterized by the scattering coefficient $\mu_s$, (b) the probability of scattering angles $\theta_s$ defined by the scattering phase function $P(\theta_s)$, and (c) the average scatter direction characterized by the first moment $g_1 = \langle \cos \theta_s \rangle$ of the scattering phase function $P(\theta_s)$. Photons that have experienced many scattering events within turbid media have lost the orientation to their original direction of travel and are considered diffuse. Diffuse remission is insensitive to the direction of individual scattering events, and can be modeled with a diffusion approximation to the radiation transport equation, which introduces the reduced scattering coefficient $\mu'_s = \mu_s(1-g_1)$ to combine the effects of scatter frequency and directionality into a single lumped parameter. Diffusion theory is generally applicable to light that remits one or two reduced scattering lengths, i.e., 1-2 $(\mu_s)^{-1}$, from the source location, which in biological tissue is approximately 1-2 millimeters.

Studies have correlated diffuse measurements of $\mu'_s(\lambda)$ with the size distribution of scattering centers in bulk tissue, providing a noninvasive characterization of biological tissue structure. However, such prior measurements are averaged over a large tissue volume and are insensitive to changes in local tissue microstructure.

Localized measurements of scatter remission have been developed to interrogate small tissue volumes of interest. When near the source, these prior art measurements collect a population of photons that have experienced few scattering events, making the signal sensitive to the direction of individual scattering events. Light in this transport regime is termed sub-diffuse. Model-based interpretation of sub-diffuse remission spectra requires both $\mu'_s$ and a parameter that describes the phase function-dependent probability of large-angle backscatter events that are likely to be collected during reflectance measurements. For forward-directed scattering media, such as in biological tissue, the relative probability of large backscattering events is proportional to the weighted ratio of the 1st and 2nd Legendre moments, $g_1$ and $g_2$, respectively, of $P(\theta_s)$. This probability is given by $\gamma=(1-g_2)/(1-g_1)$. So far, approaches that have quantitated sub-diffusion scattering parameters in biological tissue have classically been limited to the sampling of small volumes, usually sub-millimeters. In the prior art, imaging of localized scatter has been achieved by mechanically scanning a fiber optic, and results suggest that contextual interpretation of heterogeneous spatial-variations in scatter remission may discriminate between tissue types and potentially guide clinical decisions. However, these prior-art approaches can be time intensive, and studies published to date have not interpreted the signal in terms of underlying scattering properties.

Guidance of clinical decisions, for example during surgery, often requires fast assessment of large areas of tissue. This requirement has limited the translation and adoption of localized quantitative spectroscopic approaches within the clinical theatre. Recently, spatial frequency domain imaging (SFDI) has been demonstrated as a method to provide quantitative spatial maps of $\mu'_s$ and the absorption coefficient $\mu_a$ in turbid media, with fast image acquisitions over a wide field of view. See Cuccia et al. in "*Modulated imaging: quantitative analysis and tomography of turbid media in the spatial-frequency domain*", Opt. Lett. 30(11), 1354-1356 (2005), Cuccia et al. in "*Quantitation and mapping of tissue optical properties using modulated imaging*", J. Biomed. Op. 14(2), 024012 (2009), and Gioux et al. in "*First-in-human pilot study of spatial frequency domain oxygenation imaging system*", J. Biomemd. Opt. 16(8), 086015 (2011). This method applies structured light to illuminate the surface of a medium with sinusoidal intensity patterns at various spatial frequencies $f_x$. The collected signal is demodulated and optical properties are estimated from diffusion theory. The diffuse analysis invokes two important assumptions: (a) scatter dominates absorption such that $\mu'_s \gg \mu_a$, and (b) the maximum collected spatial frequency $f_x$ is limited to $0.25\mu_{tr}$ to $0.33\mu_{tr}$ (where $\mu_{tr} = \mu'_s$ for the non-absorbing case), a range of spatial frequencies that limits the sampling of photons which experience few scattering events. The first assumption has been addressed by a Monte Carlo look up table to analyze SFDI signals in highly absorbing tissues. To date, no study has directly addressed the second assumption and quantitatively analyzed sub-diffuse remission collected from structured illumination imaging, although Konecky et al., in "*Imaging scattering orientation with spatial frequency domain imaging*", J. Biomed. Opt. 16(12), 126001 (2011), considered rotation of the incident illumination pattern to identify directional preferences for scatter within a wide field of view. This unique illumination pattern was characterized as a special case of diffuse light collection that was sensitive to the anisotropic orientation of scatterers on the order of the transport length in the sampled medium, but did not yield estimates of quantitative scattering parameters.

SUMMARY

In an embodiment, a method for determining sub-diffuse scattering parameters of a material includes illuminating the material with structured light and imaging remission by the material of the structured light. The method further includes determining, from captured remission images, sub-diffuse scattering parameters of the material.

In an embodiment, a structured-light imaging system for determining sub-diffuse scattering parameters of a material includes a structured-light illuminator, for illuminating the material with structured light of periodic spatial structure, and a camera for capturing images of the remission of the structured light by the material. The structured-light imaging system further includes an analysis module for processing the images to quantitatively determine the sub-diffuse scattering parameters.

In an embodiment, a software product for analyzing images of remission of structured light, having periodic spatial structure, by a material to determine sub-diffuse scattering parameters of the material, includes machine-readable instructions encoded in non-transitory medium. The machine-readable instructions include demodulation instructions that, upon execution by a processor, process a plurality of image sets, respectively associated with a plurality of frequencies of the period spatial structure. For each of the frequencies, the corresponding image set includes a plurality of images associated with a respective plurality of spatial phase shifts of the period spatial structure. Upon execution by a processor, the demodulation instructions process the plurality of image sets to produce a respective plurality of demodulated images substantially unaffected by the periodic spatial structure and each indicating demodulated remission of the structured light at a corresponding one of the plurality of frequencies. The machine-readable instructions also include a model describing the demodulated remission as a function of (a) the reduced scattering coefficient', (b) the backscatter likelihood, and (c) the frequency of the period spatial structure. Furthermore, the machine-readable instructions include optimization instructions that, upon execution by a processor, fit the model to the demodulated remission, indicated by the demodulated images, to determine the reduced scattering coefficient and the backscatter likelihood for the material.

DETAILED DESCRIPTION OF THE EMBODIMENTS

Figure 1:
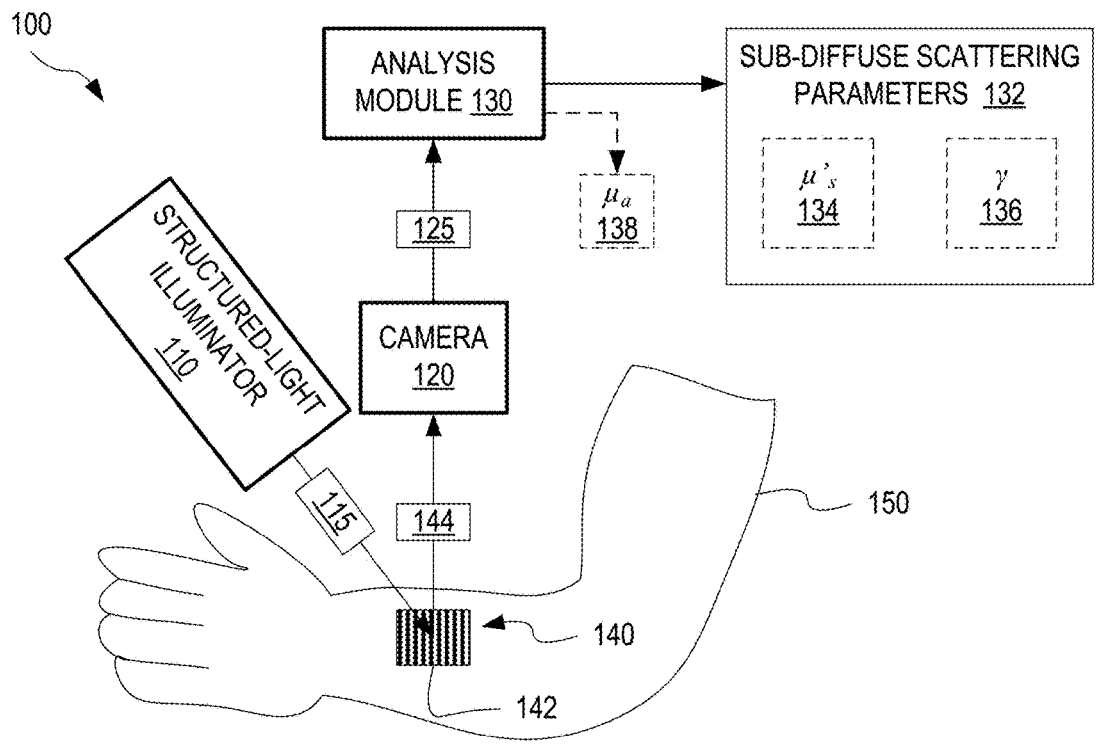
FIG. 1 illustrates a structured-light imaging system for determining sub-diffuse scattering parameters, according to an embodiment.
Figure 2:
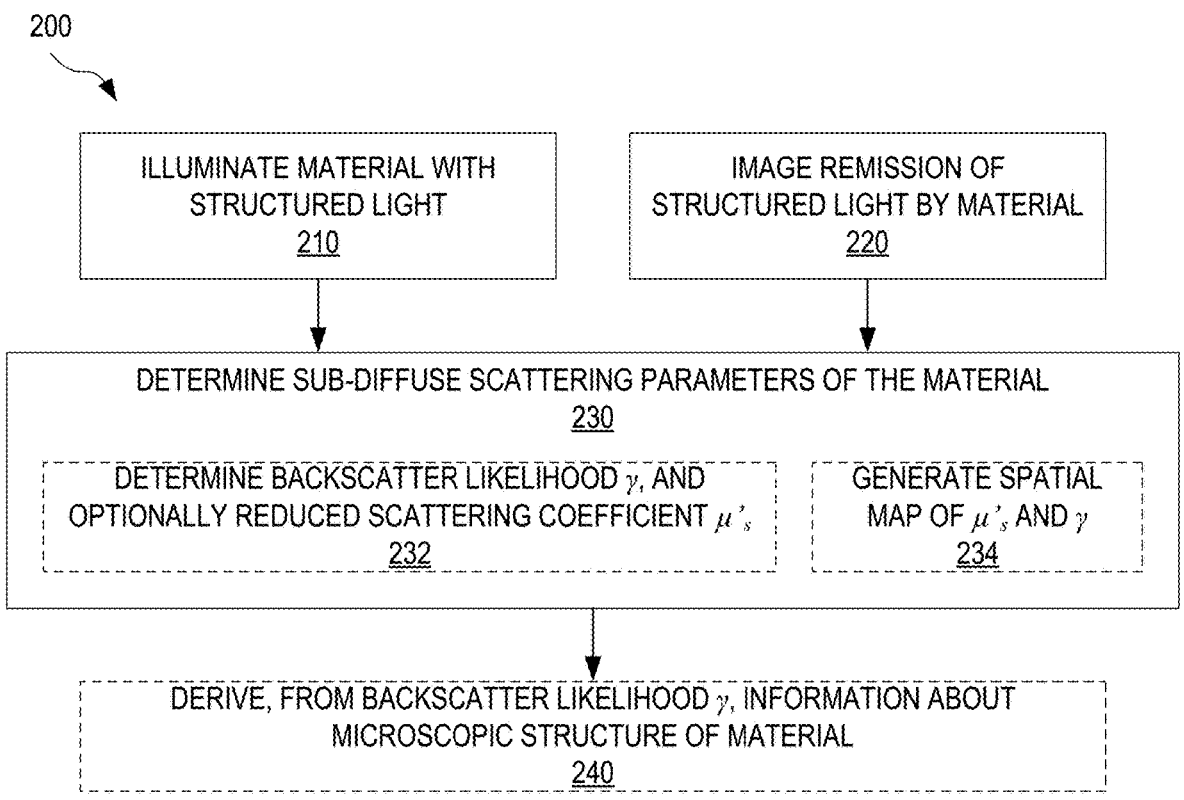
FIG. 2 illustrates a structured-light imaging method for determining sub-diffuse scattering parameters, according to an embodiment.

FIG. 1 illustrates one exemplary structured-light imaging system 100 for determining sub-diffuse scattering parameters. Structured-light imaging system 100 includes a structured-light illuminator 110, a camera 120, and an analysis module 130. FIG. 2 illustrates one exemplary structured-light imaging method 200 for determining sub-diffuse scattering parameters. Structured-light imaging system 100 implements structured-light imaging method 200. FIGS. 1 and 2 are best viewed together.

In a step 210 of structured-light imaging method 200, structured-light illuminator 110 illuminates an interrogation area 142 of a material 140 with structured light 115. Structured light 115 has a period spatial structure at interrogation area 142. In the exemplary use scenario shown in FIG. 1, material 140 is superficial tissue of a human subject 150. However, material 140 may be of a different type, including, but not limited to, (a) internal tissue of a human subject or other animal subject (for example exposed during a surgical procedure), (b) in-vivo or ex-vivo tissue of a human or other animal subject, (c) non-animal materials, (d) in-vitro cell or tissue culture, and/or (e) a fluidic sample, without departing from the scope hereof.

Figure 3:
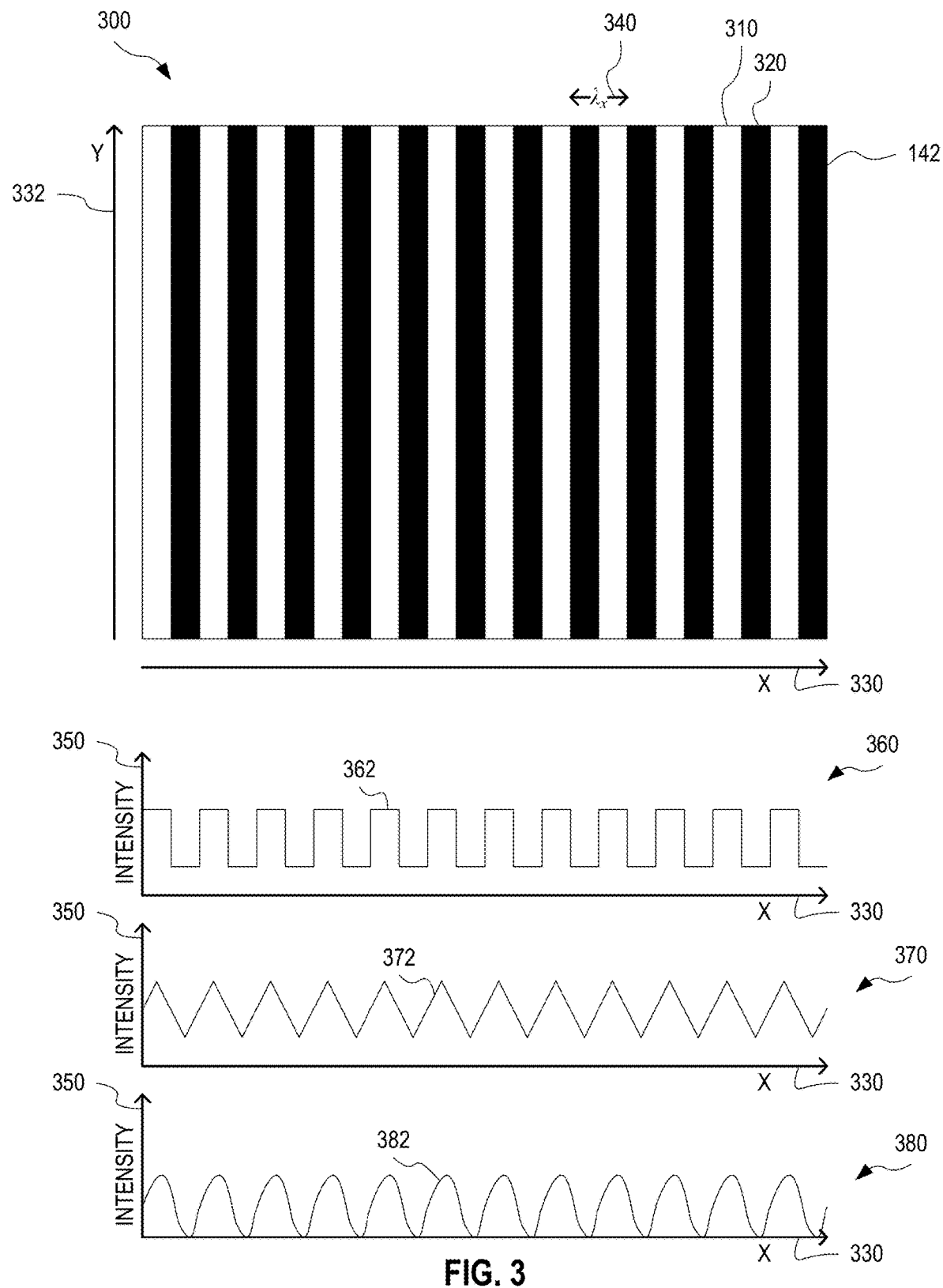
FIG. 3 illustrates periodic spatial structure of the structured light of FIGS. 1 and 2, according to an embodiment.

FIG. 3 illustrates exemplary periodic spatial structure 300 of structured light 115 at interrogation area 142 (FIG. 1). Periodic spatial structure 300 includes brighter regions 310 and darker regions 320. Brighter regions 310 and darker regions 320 alternate along an x-direction 330 to produce a characteristic spatial wavelength $\lambda_x$ (label 340) along x-direction 330. The spatial wavelength $\lambda_x$ (340) corresponds to a spatial frequency $f_x = \lambda_x^{-1}$ of periodic spatial structure 300.

Diagrams 360, 370, and 380 show exemplary line profiles of periodic spatial structure 300, plotted as intensity 350 along x-direction 330. Line-profile 362 of diagram 360 is rectangular, such that the intensity is high and substantially uniform within brighter regions 310, and low and substantially uniform within darker regions 320. Line profile 372 of diagram 370 is triangular, and line profile 382 of diagram 380 is sinusoidal.

Without departing from the scope hereof, periodic spatial structure 300 may be associated with other line profiles than rectangular, triangular, and sinusoidal. For example, periodic spatial structure 300 may have spatial structure, along x-direction 330, which is a superposition of rectangular, triangular, and/or sinusoidal. In addition, periodic spatial structure 300 may have any measurable, e.g., non-zero, contrast between brighter and darker regions 310 and 320, respectively, and the contrast between brighter and darker regions 310 and 320, respectively, may vary within interrogation area 142. While FIG. 3 shows equal contribution to periodic spatial structure 300 from brighter regions 310 and darker regions 320, brighter regions 310 may occupy a majority of periodic spatial structure 300, or darker regions 320 may occupy a majority of periodic spatial structure 300. Furthermore, while FIG. 3 shows periodic spatial structure 300 as being constant in the y-direction 332, periodic spatial structure 300 may exhibit variation along y-direction 332 without departing from the scope hereof.

Also without departing from the scope hereof, structured light 115 at interrogation area 142 may include other spatial variation superimposed on periodic spatial structure 300. Such other spatial variation may include one or more of vignetting, slow gradients, and high-frequency variation (noise for example).

Referring again to FIGS. 1 and 2, in a step 220 of structured-light imaging method 200, camera 120 images remission 144 of structured light 115 by interrogation area 142. Thus, camera 120 produces remission images 125 of interrogation area 142. Structured-light imaging method 200 concurrently performs steps 210 and 220. Herein, "remission" refers to reflection and/or scattering of light by a material, specifically the light that is scattered back from a material. Camera 120 is, for example, an imaging objective coupled with (a) a charge-coupled device (CCD) image sensor or (b) a complimentary-metal-oxide semiconductor (CMOS) image sensor.

Step 210 includes illuminating interrogation area 142 with structured light 115 having periodic spatial structure 300 (FIG. 3) with high spatial frequency $f_x >> 0.25 \mu'_s$. Remission images 125, captured in step 220, of structured light 115 having such high spatial frequencies $f_x$, sample remission in the sub-diffuse light transport regime. Generally, the spatial frequency $f_x$ of periodic spatial structure 300 determines the sensitivity to depth within the material, associated with interrogation area 142, and functions as a selection parameter for the sampled transport regime. Periodic spatial structure 300 of low spatial frequency $f_x \sim 0$ approximate a uniform wide-field illumination of interrogation area 142, and resulting remission 144 in remission images 125 is dominated by diffusely scattered light that has travelled to a wide range of depths into material 140 prior to remission. As $f_x$ is increased, periodic spatial structure 300 is preserved at increasingly shallower depths of material 140. At high spatial frequencies $f_x >> 0.25 \mu'_s$, remission images 125 contain significant contributions from sub-diffusely scattered photons. In embodiments of structured-light imaging system 100 configured to evaluate absorptive materials 140, structured-light illuminator 110 further produces periodic spatial structure 300 with a spatial frequency $f_x = 0$ or a near-zero spatial frequency $f_x$, i.e., at least nearly without periodic spatial structure, to provide a measurement of the absorption coefficient $\mu_a$ (label 138). For the purposes of the present disclosure, it is understood that determination of sub-diffuse scattering parameters 132 may be accompanied by determination of the absorption coefficient $\mu_a$ (138) based upon remission images produced with a spatial frequency $f_x = 0$ or a near-zero spatial frequency $f_x$.

Interrogation area 142 may have any extent that is practically illuminated by structured-light illuminator 110 and imaged by camera 120. In one example, interrogation area 142 is millimeter-sized. In another example, interrogation area 142 has dimensions of several centimeters. In yet another example, interrogation area 142 has dimensions compatible with structured-light imaging of a human body part or the full human body. However, interrogation area 142 may have size smaller, greater, or in between these specific sizes, without departing from the scope hereof. As compared to certain prior-art technologies that use an optical fiber to obtain a local determination of sub-diffuse scattering parameters for an essentially point-sized interrogation area, structured-light imaging method 200 facilitate wide-field imaging of sub-diffuse scattering parameters of a material, without requiring movement of any components to perform a physical scan of an extended interrogation area, such as interrogation area 142. Consequently, structured-light imaging system 100 may rapidly obtain the required data (i.e., remission images 125), which is particularly beneficial when interrogation area 142 is a portion of a human or animal subject.

In a step 230, analysis module 130 processes remission images 125 to determine sub-diffuse scattering parameters 132 of material 140. Analysis module 130 may quantitatively determine sub-diffuse scattering parameters 132. In an embodiment, step 230 includes one or both of steps 232 and 234. In step 232, analysis module 130 determines the backscatter likelihood γ (label 136) and, optionally, the reduced scattering coefficient $\mu'_s$ (label 134), based upon remission images 125. In step 234, analysis module 130 generates a spatial map of the reduced scattering coefficient $\mu'_s$ (134) and/or a spatial map of the backscatter likelihood γ (136). Such spatial maps may represent all of interrogation area 142, or one or more portions of interrogation area 142. Interrogation area 142 may have extent greater than the actual area analyzed in step 230. Although not shown in FIG. 2, step 230 may include determining absorption coefficient $\mu_a$ (138) for material 140, without departing from the scope hereof.

In an optional step 240, structured-light imaging method 200 derives, from the backscatter likelihood γ (136) determined in step 230, information about the meso/micro-scale structure of material 140. Step 240 may be performed by analysis module 130, another computer system communicatively coupled with analysis module 130, and/or by a human operator.

In one example, material 140 is an in-vivo, ex-vivo, or in-vitro tissue sample, and the information determined in step 240 may include diagnostic information about the cellular ultrastructure and/or organization of the extracellular matrix of the tissue sample. This diagnostic information may be used to identify tissue pathology such as cancer, for example for the purpose of (a) diagnosing the pathology, (b) gaining insight into tissue alterations induced by an administered therapy, and/or (c) guiding surgical resection of the pathological tissue. Step 240 may derive the diagnostic information from spatial maps of the reduced scattering coefficient $\mu'_s$ (134) and/or a spatial map of the backscatter likelihood $\gamma$ (136), which are generated in step 234. Step 240 may utilize spatial differences, including local spatial contrast, within the spatial map(s) to derive the diagnostic information. For example, pathological tissue may be characterized by sub-diffuse scattering parameters 132 that are distinctly different from those associated with healthy tissue.

In a similar example, material 140 is an in-vivo/ex-vivo/in-vitro human or other animal tissue sample, and interrogation area 142 includes a wound. In this example, step 240 may derive, from sub-diffuse scattering parameters 132, meso/micro-scale structure information pertaining to healing of the wound, quality of crosslinking-based tools used for wound repair, and/or assessment of problematic scar formation associated with keloids.

In another similar example, material 140 is in-vivo/ex-vivo/in-vitro brain tissue, for example accessed during a surgical procedure, and step 240 may derive, from sub-diffuse scattering parameters 132, meso/micro-scale structure information pertaining to pathology of the brain tissue.

In yet another example, material 140 is a non-biological material, such as a three-dimensional (3D) printed material, a liquid suspension, or a solid. In this example, step 240 derives, from sub-diffuse scattering parameters 132, an assessment of the meso/micro-scale structure of such materials, optionally to characterize fractal dimensions of the sizes of a distribution of particles in suspension, the porosity of a solid, or the texture of a surface. System 100 may implement method 200, according to this example, to verify one or more properties of a manufactured material, for example in a quality-control scenario.

In one embodiment, analysis module 130 outputs, in step 230, sub-diffuse scattering parameters 132 to a user or an external computer system. In another embodiment, analysis module 130 further performs step 240 and outputs the information about the meso/micro-scale structure of material 140, which is derived from sub-diffuse scattering parameters 132. In this embodiment, analysis module 130 may or may not output sub-diffuse scattering parameters 132. In yet another embodiment, analysis module 130 outputs the reduced scattering coefficient $\mu'_s$ (134), together with or without the backscatter likelihood $\gamma$ (136) and/or the absorption coefficient $\mu_a$ (138). This embodiment is useful for providing an accurate value of the reduced scattering coefficient $\mu'_s$ (134) at high spatial frequencies $f_x$. At high spatial frequencies $\lambda_x$, proper consideration of the backscatter likelihood $\gamma$ (136) in the sub-diffuse regime is required to accurately determine the reduced scattering coefficient $\mu'_s$ (134), as discussed below in reference to Example I. In one example, this embodiment is used to accurately determine the absorption coefficient for an absorptive material 140.

In one implementation, structured-light imaging system 100 is incorporated in a handheld device that outputs a spatial map of the backscatter likelihood $\gamma$ (136), and optionally a spatial map of the reduced scattering coefficient $\mu'_s$ (134). In another implementation, structured-light illuminator 110 and camera 120 are incorporated in one package, such as a handheld device or a surgical microscope, while analysis module is implemented on a computer in remote communication with camera 120. In yet another implementation, structured-light imaging system 100 is implemented together with another diagnostic tool, for example a flow-cytometer or a medical imaging system.

In one example of use, structured-light imaging system 100 is used as a stand-alone diagnostic tool. In another example of use, structured-light imaging system 100 is used in conjunction with one or more other diagnostic tools. In one such example, structured-light imaging system 100 determines sub-diffuse scattering parameters 132 necessary to correct a fluorescence image for distortions induced by optical properties of the material under interrogation. The fluorescence image indicates, for example, biodistribution of administered therapeutic agents. Structured-light imaging system 100 may serve to improve the accuracy of the fluorescence image. In this example of use, structured-light imaging system 100 may utilize the determination of the reduced scattering coefficient $\mu'_s$ (134) to correct remitted fluorescence signals for the distortive influence of background optical properties, providing quantitative fluorescence estimates of a fluorophore within material 140.

In certain embodiments, structured-light illuminator 110 is configured to generate structured light 115 of any one of at least two different spectral wavelengths A. With this embodiment of structured-light imaging system 100, step 230 of structured-light imaging method 200 may determine sub-diffuse scattering parameters 132 for each of these spectral wavelengths $\lambda$.

Herein, the "backscatter likelihood $\gamma$" refers to the parameter $\gamma=(1-g_2)/(1-g_1)$ of the scattering phase function $P(\theta_s)$. However, without departing from the scope hereof, the backscatter likelihood $\gamma$ may be replaced by another parameter, or another set of parameters, that is sensitive to the backscatter likelihood. In one example, the backscatter likelihood $\gamma$ is constituted by, or includes, a summation of multiple Legendre moments of the phase function. The backscatter likelihood $\gamma$ may also be expressed in terms of the fractal dimension of the imaged particles.

Figure 4:
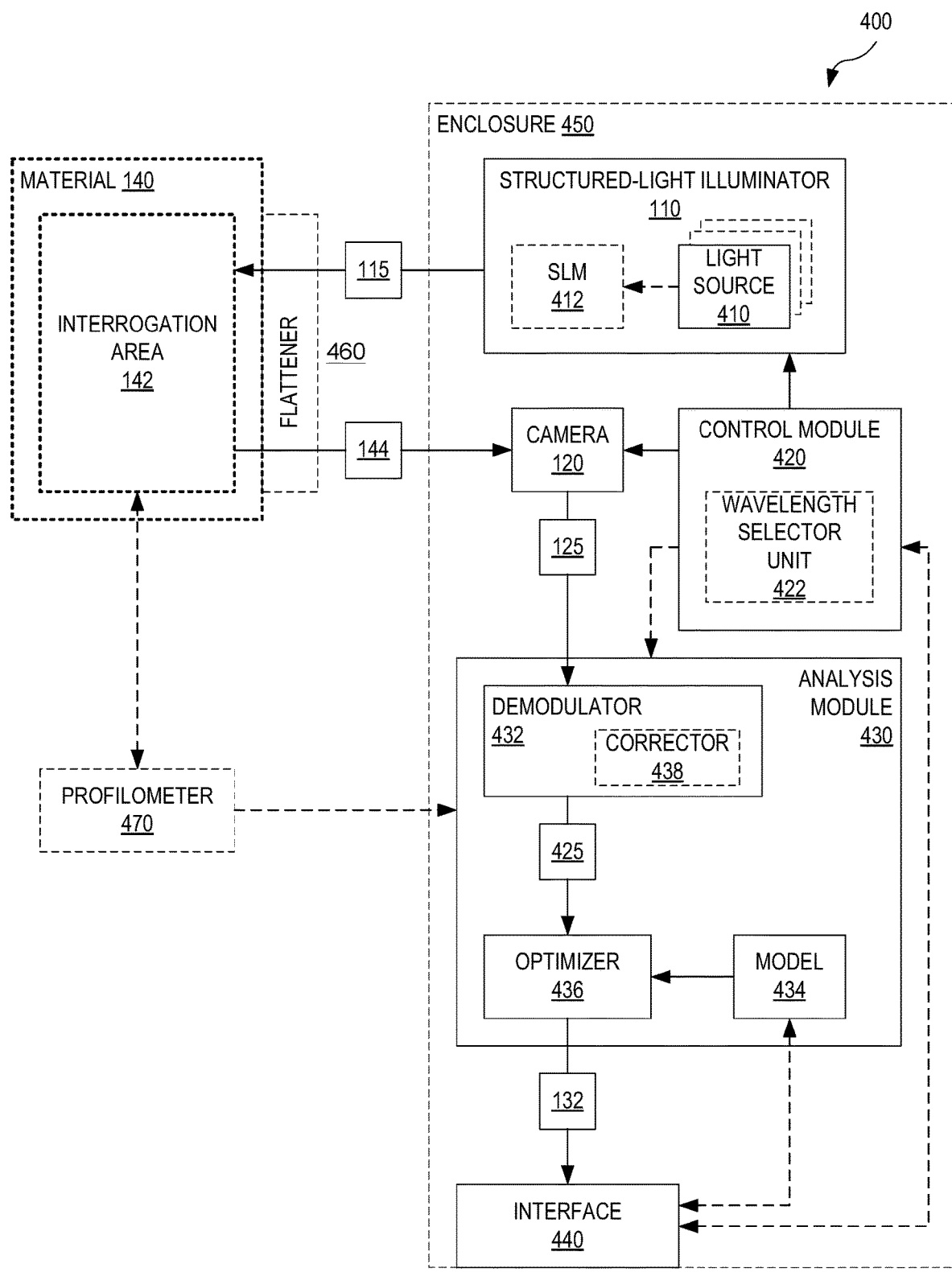
FIG. 4 illustrates a structured-light imaging system for quantitatively determining sub-diffuse scattering parameters, according to an embodiment.

FIG. 4 illustrates one exemplary structured-light imaging system 400 which is an embodiment of structured-light imaging system 100 (FIG. 1). Structured-light imaging system 400 includes structured-light illuminator 110, camera 120, an analysis module 430, an interface 440, and a control module 420.

Structured-light imaging system 400 implements structured-light illuminator 110 with at least one light source 410 and, optionally, a spatial light modulator (SLM) 412 that imposes a periodic spatial structure on light emitted by light source(s) 410. SLM 412 is for example a liquid-crystal panel or a digital mirror device. Structured-light illuminator 110 may be implemented as a digital light projector.

Control-module 420 controls structured-light illuminator 110 to generated structured light 115 with periodic spatial structure 300 of a desired spatial frequency $f_x$. Control-module 420 and structured-light illuminator 110 cooperate such that periodic spatial structure 330 may have any one of at least two different spatial frequencies $f_x$, wherein the at least two different spatial frequencies $f_x$ include (a) at least one lower spatial frequency $f_x$ that is sensitive to the reduced scattering coefficient $\mu'_s$ and (b) at least one higher spatial frequency $f_x$ that is sensitive to the backscatter likelihood $\gamma$. In embodiments of structured-light imaging system 400 configured to evaluate absorptive materials 140, control-module 420 and structured-light illuminator 110 are further configured to cooperate to produce periodic spatial structure 330 with a spatial frequency $f_x=0$, i.e., without periodic spatial structure. For each spatial frequency $f_x \neq 0$, control module 420 is further configured to control a spatial phase shift $\phi$ of periodic spatial structure 330. Control module 420 is thus capable of spatially modulating periodic spatial structure 300. Control module 420 may achieve the desired spatial frequencies $f_x$ and spatial phase shifts ϕ by adjusting SLM 412. Control module 420 also controls camera 120 to capture remission images 125 at desired spatial frequencies $f_x$ and spatial phase shifts ϕ of periodic spatial structure 300.

In an embodiment, structured-light imaging system 400 is configured to determine sub-diffuse scattering parameters 132 for a plurality of spectral wavelengths λ. In this embodiment, structured-light illuminator 110 includes a plurality of light sources 410, each configured to emit light at a different spectral wavelength λ, and control module 420 includes a wavelength selector unit 422 that selects a desired one of the plurality of light sources 410. Without departing from the scope hereof, structured-light illuminator 110 may instead of the plurality of light sources 410, or in combination therewith, include spectral filters that select desired spectral wavelengths λ.

Analysis module 430 is an embodiment of analysis module 130, and includes a demodulator 432, a model 434, and an optimizer 436. Demodulator 432 spatially demodulates remission images 125 to generate demodulated remission images 425 that are substantially unaffected by periodic spatial structure 300 of structured light 115. Optionally, demodulator 432 includes a corrector 438 that corrects demodulated remission images 425 for spatial non-uniformities that are different from periodic spatial structure 300 and that is induced by one or both of structured-light illuminator 110 and camera 120. Model 434 describes demodulated remission as a function of sub-diffuse scattering parameters 132 and the spatial frequency $f_x$ of periodic spatial structure 300. Optimizer 436 fits model 434 to demodulated remission images 425 to determine sub-diffuse scattering parameters 132. Optimizer 436 communicates sub-diffuse scattering parameters 132 to interface 440.

In one implementation, analysis module 430 is communicatively coupled with control module 420. In this implementation, control module 420 may communicate relevant information, such as spatial frequencies $f_x$, spatial phases ϕ, and/or spectral wavelengths λ associated with remission images 125. Analysis module 430 may utilize this information to process remission images 125 and/or demodulated remission images 425.

Interface 440 communicates results generated by structured-light imaging system 400 to a user or a remote location such as a remote computer. Interface 440 may include one or more of (a) a display that displays data generated by analysis module 430 and/or camera 120, (b) a wireless interface (e.g., WiFi, Bluetooth, cellular network, and/or wireless USB) that transfers such data to a remote location, (c) a wired interface (e.g., Ethernet, USB, FireWire, and/or Thunderbolt) that transfers such data to a remote location. Interface 440 may further be configured to receive instructions from a user or an external system. For example, interface 440 may receive instructions to control at least aspects of the functionality of control module 420. Interface 440 may also receive instructions used by analysis module 430, such as model 434. Additionally, interface 440 may output settings of control module 420 and/or analysis module 430.

In an embodiment, structured-light imaging system 400 includes an enclosure 450. Enclosure 450 has ports for outputting structured light 115 and receiving remission 144.

In one implementation, structured-light imaging system 400 includes a flattener 460, or is configured to cooperate with flattener 460. Flattener 460 is a substrate capable of at least partially transmitting light of the spectral wavelengths λ produced by structured-light illuminator 110. Flattener 460 has a substantially planar surface which is pressed against material 140 to flatten material 140 within interrogation area 142, to eliminate artifacts in remission images 125 caused by non-flatness of material 140 within interrogation area 142. In an alternative implementation, structured-light imaging system 400 includes a profilometer 470 or is configured to cooperate with profilometer 470. Profilometer 470 evaluates the surface profile of material 140 within interrogation area 142. Profilometer 470 communicates surface profile measurements to analysis module 430, such that analysis module 430, for example demodulator 432, may correct remission images 125 or demodulated remission images 425 to eliminate or reduce artifacts caused by non-flatness of material 140 within interrogation area 142.

Without departing from the scope hereof, analysis module 430 may exist as a stand-alone system independent from structured-light illuminator 110, camera 120, control module 420, and interface 440. This embodiment of analysis module 430 may be implemented as machine-readable instructions, encoded on non-transitory medium, which, upon execution by a processor, process remission images 125, as discussed below in reference to FIG. 5, to determine sub-diffuse scattering parameters 132.

Figure 5:
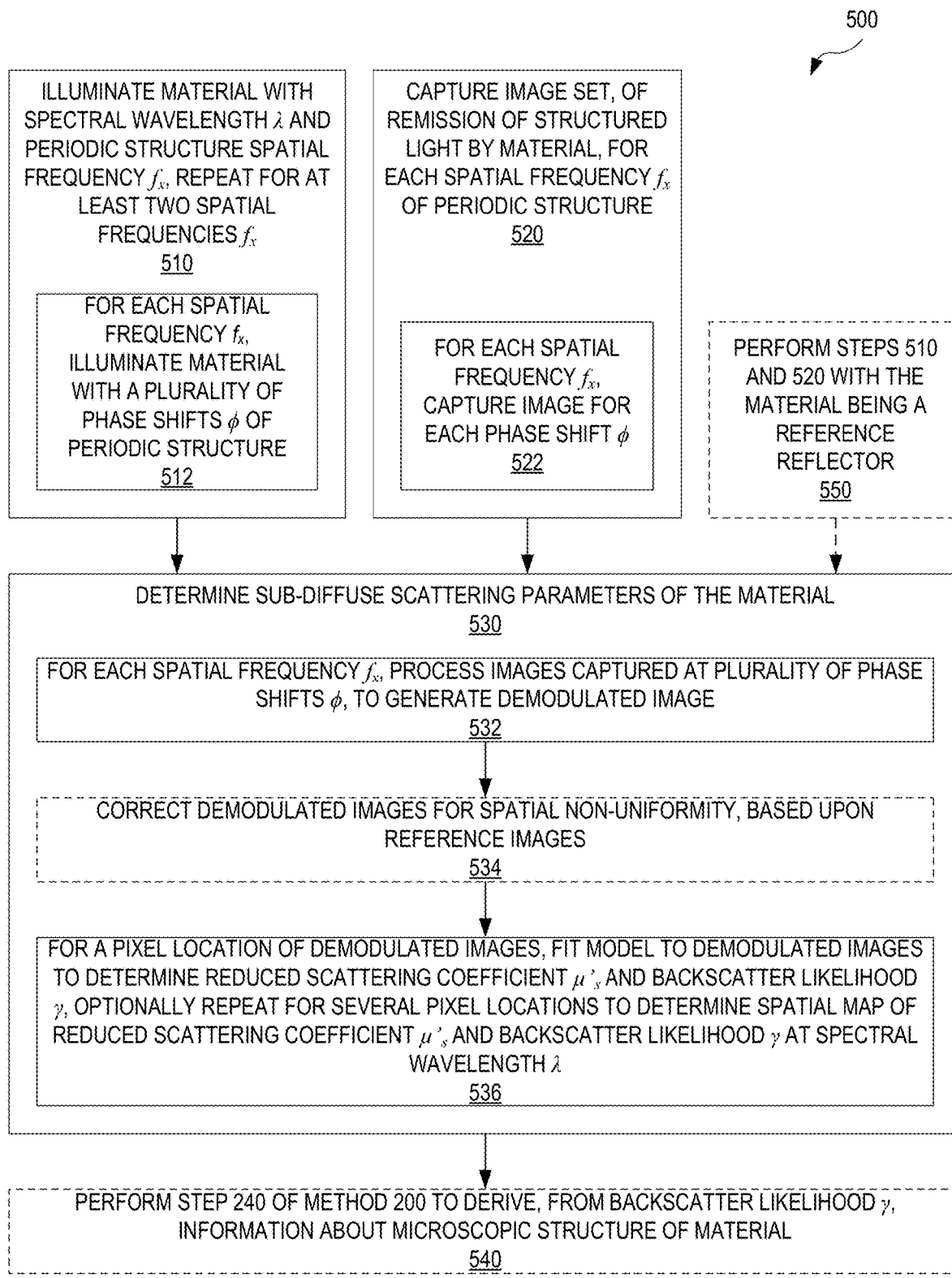
FIG. 5 illustrates a structured-light imaging method for quantitatively determining sub-diffuse scattering parameters, according to an embodiment.

FIG. 5 illustrates one exemplary structured-light imaging method 500 for quantitatively determining sub-diffuse scattering parameters 132 (FIG. 1), specifically the reduced scattering coefficient $μ'_s$ (134) and the backscatter likelihood γ (136), at a spectral wavelength λ. Structured-light imaging method 500 is an embodiment of structured-light imaging method 200 (FIG. 2) and may be performed by structured-light imaging system 400 (FIG. 4).

In a step 510, a material is illuminated with structured light of spectral wavelength λ, and at least two different spatial frequencies $f_x$ of the periodic structure, wherein the two spatial frequencies $f_x$ are applied in series. For each spatial frequency, step 510 includes a step 512 of illuminating, in series, the material with a plurality of spatial phase shifts ϕ of the periodic structure. Thus, step 512 spatially modulates the periodic structure on the material. In one example of step 510 and step 512, control module 420 controls structured-light illuminator 110 to produce structured light 115 with spectral wavelength 2 and with periodic structure 300 of spatial frequency $f_x$. Control module 420 further controls structured-light illuminator 110 to temporally adjust the spatial phase shift ϕ of periodic structure 300 to spatially modulate periodic structure 300 on interrogation area 142 of material 140. Control module 420 repeats this operation for at least two different spatial frequencies $f_x$ including (a) at least one lower spatial frequency $f_x$ that is sensitive to the reduced scattering coefficient $μ'_s$ and (b) at least one higher spatial frequency $f_x$ that is sensitive to the backscatter likelihood γ. Control module 420 may further control structured-light illuminator 110 to produce structured light 115 without periodic spatial structure 300, i.e., with a spatial frequency $f_x=0$.

Concurrently with step 510, structured-light imaging method 500 performs a step 520. Step 520 captures a plurality of image sets of remission by the material of the structured light applied in step 510. Specifically, for each spatial frequency $f_x$ applied in step 510, step 520 performs a step 522 to produce an image set associated with the spatial frequency $f_x$ under consideration. For each such spatial frequency, step 520 invokes step 522 to capture an image for each spatial phase shift ϕ of the periodic structure, thus producing the image set associated with the spatial frequency $f_x$ under consideration. Each such image set captures an associated spatial modulation applied in step 512. In one example of steps 520 and 522, control module 420 controls camera 120 to capture a remission image 125 for each spatial frequency $f_x$ and for each spatial phase shift $\phi$ associated with each spatial frequency, wherein the spatial frequencies $f_x$ and the spatial phase shifts $\phi$ are those applied in step 510 and 512.

In a step 530, method 500 determines sub-diffuse scattering parameters of the material. Step 530 includes steps 532 and 536. In step 532, method 500 processes each of the plurality of image sets captured in step 520, using step 522, to generate a demodulated image for each of the spatial frequencies $f_x$. Specifically, for each spatial frequency $f_x$, step 532 processes the associated image set (i.e., the plurality of images respectively associated with the plurality of spatial phase shifts $\phi$ applied at the spatial frequency $f_x$) to generate a demodulated image that is substantially unaffected by the periodic structure of the structured light applied in step 510. In one example of step 532, demodulator 432 processes, for each spatial frequency $f_x$, remission images 125 captured at the plurality of spatial phases $\phi$, to produce demodulated remission image 425 associated with the spatial frequency $f_x$.

Method 500 may utilize a variety of spatial phase shifts $\phi$ to achieve the demodulation. In one embodiment, the structured light, applied in step 512 and associated with either one of the spatial frequencies $f_x$, is of the form $$I_i(x,y,f_x) = \sin(f_x x + \phi_i + \phi_0),$$

wherein $\phi_i = [0, 2\pi/3, 4\pi/3]$ for respective i=[1,2,3]; and $\phi_0$ is an arbitrary phase that is the same for all i. $\phi_0$ may be zero. In this embodiment, step 530 determines the demodulated remission image (e.g., demodulated remission image 425), associated with spatial frequency $f_x$, as $$M_{AC}(x_i, f_x) = A \sqrt{\begin{array}{l}(M_1(x_i, f_x) - M_2(x_i, f_x))^2 + \\ (M_1(x_i, f_x) - M_3(x_i, f_x))^2 + \\ (M_2(x_i, f_x) - M_3(x_i, f_x))^2\end{array}},$$

wherein A is a proportionality constant; $M_1$, $M_2$, and $M_3$ are remission images (e.g., remission images 125) respectively captured for the spatial phases $\phi_1$, $\phi_2$, and $\phi_3$; and $x_i$ is a pixel location in the remission images $M_1$, $M_2$, and $M_3$, and in the demodulated remission image $M_{AC}$. Step 530 calculates $M_{AC}(x_i, f_x)$ at each pixel location $x_i$. Step 530 may further determine a corresponding spatially variant DC amplitude as $$M_{DC}(x_i, f_x) = B(M_1(x_i, f_x)^2 + M_2(x_i, f_x)^2 + M_3(x_i, f_x)^2),$$

wherein B is a proportionality constant.

In another embodiment, the structured light, applied in step 512 and associated with either one of the spatial frequencies $f_x$, is of the form $$I_j(x,y,f_x) = \sin(f_x x + \phi'_i + \phi'_0),$$

wherein $\phi'_i = [0, 2\pi/N, \ldots, (N-1)2\pi/N]$ for respective $i=1, \ldots, N$; N is an integer greater than two; and $\phi'_0$ is an arbitrary phase that is the same for all i. $\phi'_0$ may be zero. In this embodiment, step 530 determines the demodulated remission image (e.g., demodulated remission image 425), associated with spatial frequency $f_x$, in a fashion similar to that used for phases $\phi_i = [0, 2\pi/3, 4\pi/3]$, discussed above.

In step 536, method 500 fits a predetermined model to the plurality of demodulated images determined in step 532 for the respectively plurality of spatial frequencies $f_x$. The model describes demodulated remission as a function of the reduced scattering coefficient $\mu'_s$, the backscatter likelihood $\gamma$, and the spatial frequency $f_x$, at the spectral wavelength $\lambda$ of the structured light applied in step 510. For each pixel location of interest, step 536 performs an optimization to fit the model corresponding to the plurality of demodulated remissions respectively associated with the plurality of spatial frequencies $f_x$ applied in step 510. Each such optimization yields a determination of the reduced scattering coefficient $\mu'_s$ and the backscatter likelihood $\gamma$ at this pixel location and at the spectral wavelength $\lambda$ of the structured light. The pixel location corresponds to a physical location of the material interrogated by method 500.

In one embodiment, step 536 performs the optimization for one selected pixel location of interest to determine the reduced scattering coefficient $\mu'_s$ and the backscatter likelihood $\gamma$ at this selected pixel location. In another embodiment, step 536 performs the optimization for each of a plurality of pixel locations of interest to determine the reduced scattering coefficient $\mu'_s$ and the backscatter likelihood $\gamma$ at each of the plurality of pixel locations of interest. This plurality of pixels may represent all pixel locations of the remission images captured in step 520 or a subset thereof. The subset, for example, corresponds to a selected region of interest and/or to a plurality of spatially separated pixel locations of interest.

In one implementation of step 536, the model (e.g., model 434) is of the form $$R_{d,model}(\mu'_s, \gamma, f_x) = \eta \left(1 + (\zeta_4 \gamma^{-2})(\mu'_s f_x^{-1})^{(-\zeta_3 \gamma)}\right) \left[\frac{(\mu'_s f_x^{-1})^{(-\zeta_2 \gamma)}}{\zeta_1 \gamma^2 + (\mu'_s f_x^{-1})^{(-\zeta_2 \gamma)}}\right],$$

wherein $R_{d,model}$ is the modeled demodulated remission, $\eta$ is a fitting parameter, and $\zeta_i$, i=1, 2, 3, and 4, are fitting parameters. $\eta$ is related to, at least, the collection efficiency of the camera (e.g., camera 120). $\zeta_i$ are related to, at least, dynamics in demodulated remission observed in response to changes in (a) so-called dimensionless scattering $\mu'_s f_x^{-1}$ and (b) the backscatter likelihood $\gamma$. Without departing from the scope hereof, $R_{d,model}$ may be of an analytical form different from the one provided herein, or $R_{d,model}$ may be non-analytical and provided as a lookup table, for example.

In one example of step 536, optimizer 436 fits model 434, for each of one or more pixel locations of interest, to the demodulated remission indicated by a plurality of demodulated remission images 425 respectively associated with the plurality of spatial frequencies $f_x$ applied in step 510. In this example, model 434 describes demodulated remission as a function of the reduced scattering coefficient $\mu'_s$, the backscatter likelihood $\gamma$, and the spatial frequency $f_x$, at the spectral wavelength $\lambda$ of the structured light applied in step 510. Optimizer 436 thus determines the reduced scattering coefficient $\mu'_s$ (134) and the backscatter likelihood $\gamma$ (136) for spectral wavelength $\lambda$ of structured light 115 at each considered pixel location. Without departing from the scope hereof, analysis module 430 may, prior to performing step 536, bin together adjacent pixels of remission images 125 or demodulated remission images 425 to spatially average remission to reduce noise.

In an embodiment, method 500 includes steps 550 and 534. Steps 550 and 534 cooperate to correct the demodulated images, generated in step 532, for spatial non-uniformity that is different from the periodic structure of the structured light and that is introduced by one or both of (a) structured-light illuminator used in step 510 and (b) the camera used in step 520. Step 550 performs the same operations as performed in steps 510 and 520 for a material that is a reference reflector with known optical properties. For example, the reference reflector is a reflector with known and spatially uniform reflectivity properties along its surface. In one example of step 550, structured-light imaging system 400 performs steps 510 and 520 with material 140 being a reference reflector. The reference reflector may be a siloxane titanium dioxide reflectance standard, or a material with known sub-diffuse scattering parameters, such as a material with known reduced scattering coefficient $\mu'_s$ and known backscatter likelihood $\gamma$. In this embodiment of method 500, step 532 includes processing images captured in step 550 to produce demodulated remission images $M_{AC}^{ref}(x_i, f_x)$ for the reference reflector. In step 534, the demodulated remission images $M_{AC}(x_i, f_x)$ pertaining to the actual material under interrogation are corrected to produce corrected, demodulated remission images $$R_d(x_i, f_x) = \frac{M_{AC}(x_i, f_x)}{M_{AC}^{ref}(x_i, f_x)} R_d^{ref}(x_i, f_x),$$

wherein $R_d^{ref}(x_i, f_x)$ is a calibration coefficient. For example, $R_d^{ref}(x_i, f_x)$ is informed by Monte Carlo simulations as discussed by Laughney et al. in "*System analysis of spatial frequency domain imaging for quantitative mapping of surgically resected breast tissue*", J. Biomed. Opt. 13(4), 041302 (2008), which is incorporated by reference herein in its entirety. In this embodiment of method 500, step 536 fits the model to $R_d(x_i, f_x)$. In one example of step 534, corrector 438 corrects demodulated remission images 425 before demodulator 432 communicates demodulated remission images 425 to optimizer 436. In embodiments of method 500, which do not include step 534, step 536 fits the model to $M_{AC}(x_i, f_x)$.

In an optional step 540, method 500 performs step 240 of structured-light imaging method 200 to derive, from the backscatter likelihood $\gamma$ determined in step 536, information about meso/micro-scale structure of the material.

Without departing from the scope hereof, step 530 may be implemented as a stand-alone method for analyzing structured-light images of a material to determine the reduced scattering coefficient $\mu'_s$ and the backscatter likelihood $\gamma$ (136) for spectral wavelength $\lambda$ of the structured light. Step 530 is, for example, implemented as machine-readable instructions encoded on non-transitory medium and executable by a processor.

Figure 6:
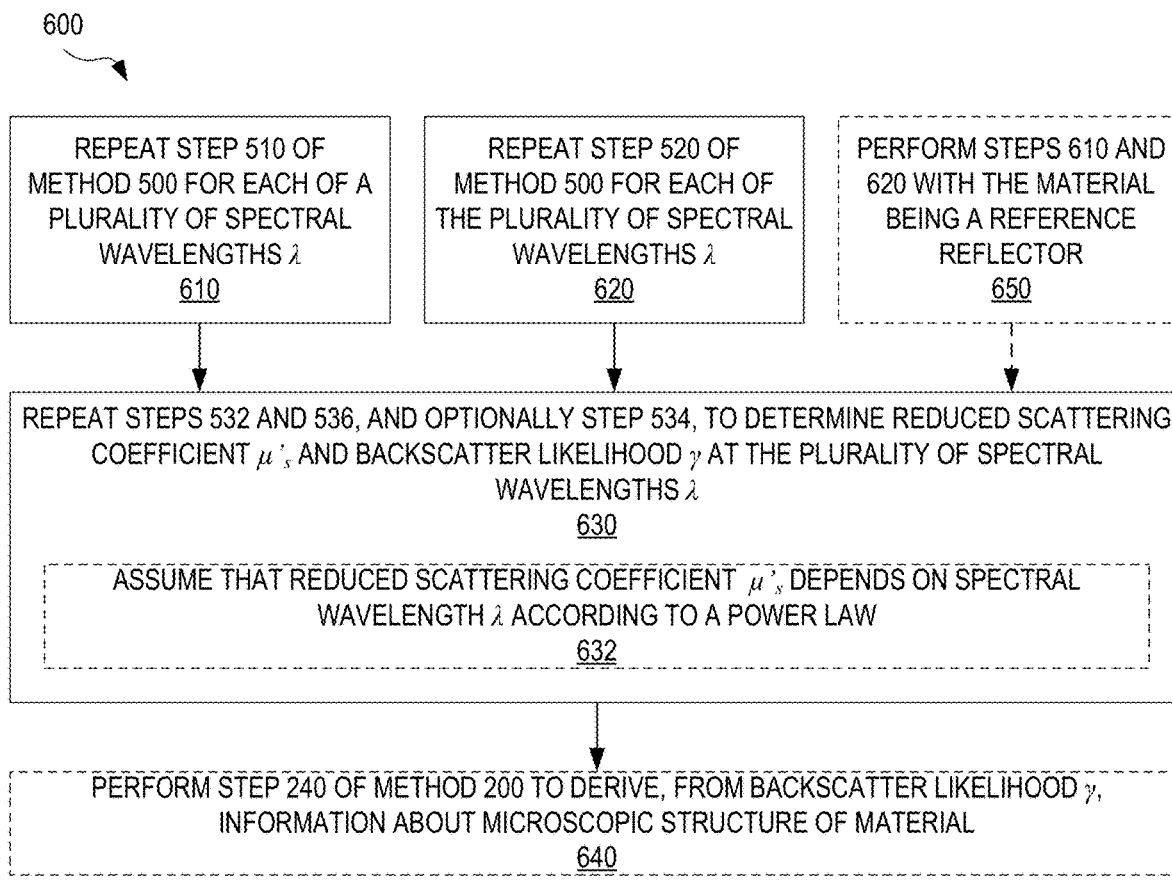
FIG. 6 illustrates a structured-light imaging method for quantitatively determining sub-diffuse scattering parameters at a plurality of spectral wavelengths, according to an embodiment.

FIG. 6 illustrates one exemplary structured-light imaging method 600 for quantitatively determining sub-diffuse scattering parameters 132 (FIG. 1), specifically the reduced scattering coefficient $\mu'_s$ (134) and the backscatter likelihood $\gamma$ (136), at a plurality of spectral wavelengths $\lambda$. Structured-light imaging method 600 is an extension of structured-light imaging method 500 (FIG. 5) to multiple spectral wavelengths $\lambda$. Structured-light imaging method 600 may be performed by structured-light imaging system 400 (FIG. 4).

In a step 610, method 600 repeats step 510 of method 500 for a plurality of spectral wavelengths $\lambda$. In one example of step 610, control module 420 activates, in series, different light sources 410, each emitting light at a different spectral wavelength $\lambda$.

In a step 620, method 600 repeats step 520 of method 500 for each of the plurality of spectral wavelengths $\lambda$ applied in step 610, as discussed in reference to FIG. 5.

In a step 630, method 600 repeats steps 532 and 536 for each of the plurality of spectral wavelengths $\lambda$ applied in step 610. Step 630 utilizes a model of the remission (e.g., model 434), which is valid for all of the spectral wavelengths $\lambda$. Step 630 thus determines the reduced scattering coefficient $\mu'_s$ and the backscatter likelihood $\gamma$ at each of the plurality of spectral wavelengths $\lambda$. The model used in step 630 is, for example, $R_{d,model}(\mu'_s, \gamma, f_x)$ discussed above in reference to FIG. 5, with wavelength-dependent reduced scattering coefficient $\mu'_s(\lambda)$ and wavelength-dependent backscatter likelihood $\gamma(\lambda)$.

In an embodiment, step 630 includes a step 632 of assuming that the reduced scattering coefficient $\mu'_s$ depends on the spectral wavelengths $\lambda$ according to a power law $\mu'_s(\lambda)=a(\lambda/\lambda_0)^{-b}$, wherein $\lambda_0$ is a reference wavelength, and a and b are fitting parameters of the model (e.g., model 434). In one example, step 630 is applied to four different spectral wavelengths $\lambda$ and step 630, with step 632 included therein, optimizes six different parameters: a and b, and the backscatter likelihood $\gamma(\lambda)$ for each of the four spectral wavelengths.

In an embodiment, method 600 includes a step 650, and step 630 further performs step 534 as discussed in reference to FIG. 5. Step 650 performs step 610 and 620 with the material being a reference reflector, as discussed in reference to FIG. 5 but extended to the plurality of spectral wavelengths $\lambda$. In this embodiment, step 630 further includes performing step 534, for each of the spectral wavelengths $\lambda$, to correct the demodulated remission images for spatial non-uniformity that is different from periodic spatial structure 300 and that is induced by one or both of (a) structured-light illuminator used in step 610 and (b) the camera used in step 620.

Figure 7:
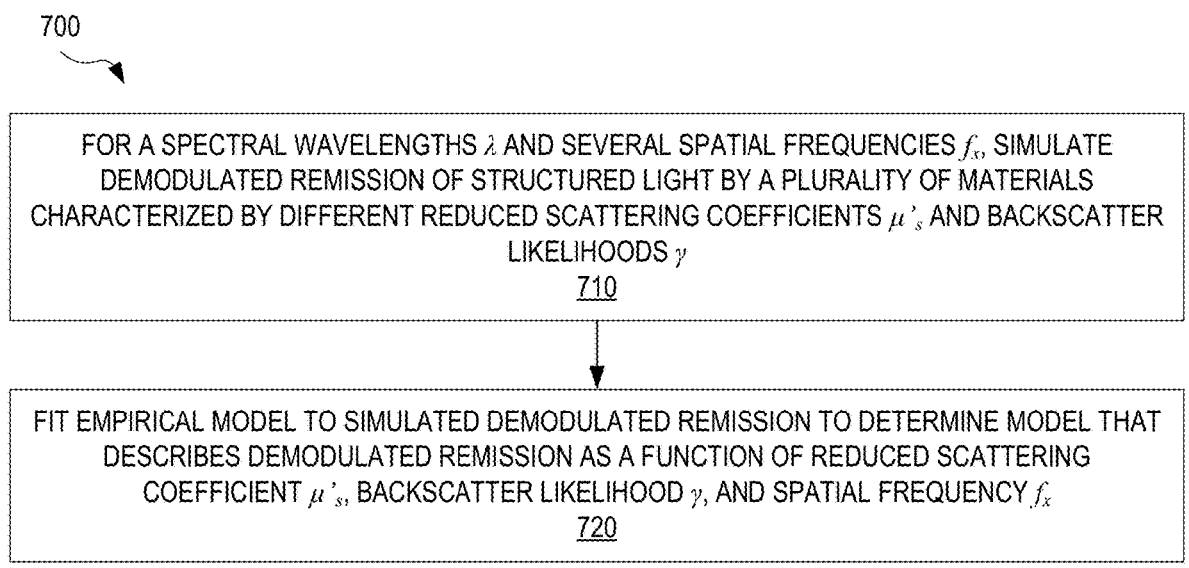
FIG. 7 illustrates a method for determining a model describing demodulated remission as a function of sub-diffuse scattering parameters and spatial frequency of structured light, according to an embodiment.

FIG. 7 illustrates one exemplary method 700 for determining the model used in step 536 of method 500 (FIG. 5), for example model 434 of structured-light imaging system 400 (FIG. 4).

A step 710 simulates demodulated remission of structured light by a plurality of materials being characterized by different values of the reduced scattering coefficient $\mu'_s$ and the backscatter likelihood $\gamma$. Step 710 performs the simulation for a plurality of spatial frequencies $f_x$ and a spectral wavelength $\lambda$. In one example of step 710, the simulation is a Monte Carlo simulation.

A step 720 considers an empirical model describing demodulated remission $R_d$ as a function of (a) the reduced scattering coefficient $\mu'_s$ and (b) the backscatter likelihood $\gamma$, (c) the spatial frequency $f_x$, and (d) at least one fitting parameter. The at least one fitting parameter is optimized to fit the empirical model to the simulation results generated in step 710, thus determining a model that describes demodulated remission $R_d$ as a function of only three unknown parameters: the reduced scattering coefficient $\mu'_s$, the backscatter likelihood $\gamma$, and the spatial frequency $f_x$. In one example of step 720, this model is $R_{d,model}(\mu'_s, \gamma, f_x)$ which is discussed above in reference to FIG. 5.

Figure 8:
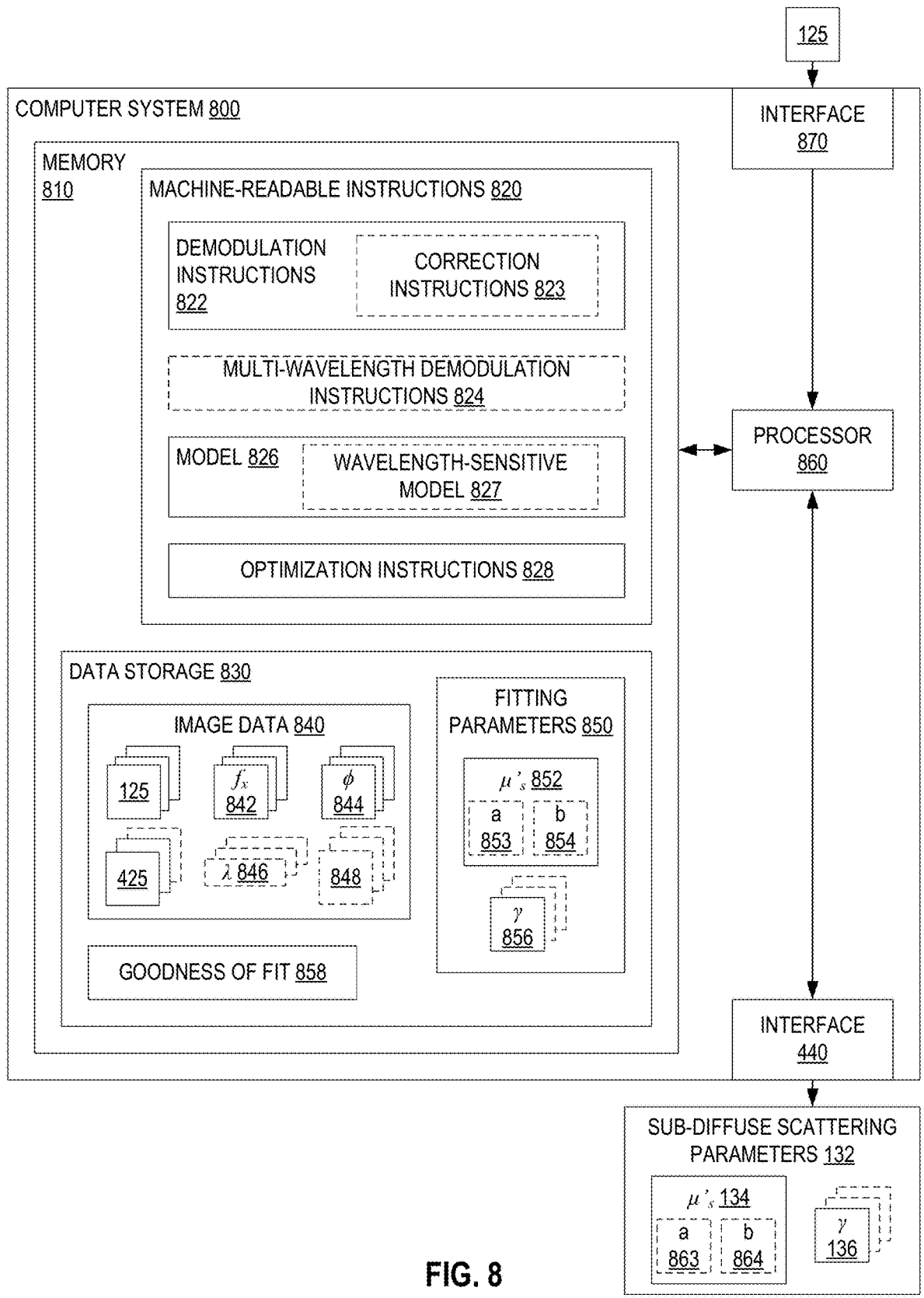
FIG. 8 illustrates a computer system for processing structured-light remission images to determine sub-diffuse scattering parameters, according to an embodiment.

FIG. 8 illustrates one exemplary computer system 800 that implements step 530 of structured-light imaging method 500 (FIG. 5), and/or implements step 630 of structured-light imaging method 600 (FIG. 6). Computer system 800 is an embodiment of analysis module 430 of structured-light imaging system 400 (FIG. 4).

Computer system 800 includes a memory 810, a processor 860, an interface 870, and interface 440 (FIG. 4). Processor 860 is communicatively coupled with interfaces 870 and 440, and with memory 810. Interface 870 may include one or both of a wireless interface (e.g., WiFi, Bluetooth, cellular network, and/or wireless USB) and a wired interface (e.g., Ethernet, USB, FireWire, and/or Thunderbolt). Memory 810 is, for example, of type ROM, Flash, magnetic tape, magnetic drive, optical drive, RAM, other non-transitory medium, or combinations thereof.

Memory 810 includes (a) machine-readable instructions 820 encoded in a non-transitory portion of memory 810 and (b) a data storage 830. Machine-readable instructions 820 include demodulation instructions 822 that, upon execution by processor 860 perform step 532 of method 500. Optionally, demodulation instructions 822 include correction instructions that, upon execution by processor 860 perform step 534 of method 500. Machine-readable instructions 820 further include a model 826 that describes demodulated remission as a function of the reduced scattering coefficient $\mu'_s$, the backscatter likelihood $\gamma$, and the spatial frequency $f_x$. Model 826 implements model 434 and is, for example, $R_{d,model}(\mu'_s, \gamma, f_x)$ which is discussed above in reference to FIG. 5. Optionally, model 826 includes a wavelength-sensitive module 827. For example, model 827 may include $R_{d,model}(\mu'_s, \gamma, f_x)$ and power law $\mu'_s(\lambda) = a(\lambda/\lambda_0)^{-b}$ discussed above in reference to FIG. 6. Machine-readable instructions 820 also include optimization instructions 828 that, upon execution by processor 860, fit model 826 to demodulated remission images 425. Additionally, machine-readable instructions 820 may include multi-wavelength demodulation instructions 824 that, upon execution by processor 860, apply demodulation instructions 822 to remission images 125 associated with a plurality of spectral wavelengths $\lambda$.

Data storage 830 includes an image data storage 840, to which processor 860 may store remission images 125, corresponding spatial frequencies $f_x$ (label 842), corresponding phase shifts $\phi$ (label 844), corresponding spectral wavelengths $\lambda$ (label 846), demodulated remission images 425, and optionally spatial maps 848 of the reduced scattering coefficient $\mu'_s$ and/or the backscatter likelihood $\gamma$. Data storage 830 also includes fitting parameters 850 with fitting parameters 852 and 856 to which processor 860 may store temporary and/or final fitting parameters for the reduced scattering coefficient $\mu'_s$ and the backscatter likelihood $\gamma$, respectively. Optionally, fitting parameter 852 includes fitting parameters a (label 853) and b (label 854) pertaining to the power law $\mu'_s(\lambda) = a(\lambda/\lambda_0)^{-b}$. Furthermore, data storage 830 includes a goodness of fit parameter 858 to which processor 860 may store one or more values for a metric that represents the goodness of fit of model 826 to demodulated remission images 425.

In operation, processor 860 receives remission images 125 via interface 870 and stores remission images 125 to image data storage 840. Processor 860 may also receive corresponding spatial frequencies $f_x$ (label 842), corresponding phase shifts $\phi$ (label 844), and corresponding spectral wavelengths $\lambda$ (label 846) from either interface 870 or interface 440. Alternatively, corresponding spatial frequencies $f_x$ (label 842), corresponding phase shifts $\phi$ (label 844), and corresponding spectral wavelengths $\lambda$ (label 846) are stored to image data storage 840 by another processor, for example before memory 810 is coupled with processor 860. Next, processor 860 executes machine-readable instructions according to step 530 of method 500 or according to step 630 of method 600. During this execution, processor may utilize data storage 830 to store data to and retrieve data from image data storage 840, fitting parameters 850, and/or goodness of fit 858. Processor 860 outputs sub-diffuse scattering parameters 132 via interface 440. For example, processor 860 outputs the reduced scattering coefficient $\mu'_s$ (134) and the backscatter likelihood $\gamma$ (136) for each spectral wavelengths $\lambda$ processed by computer system 800. Processor 860 may output the reduced scattering coefficient $\mu'_s$ (134) in the form of final results for fitting parameters a (label 863) and b (label 864). In one example of operation, processor 860 outputs spatial map(s) 848 of the reduced scattering coefficient $\mu'_s$ and/or the backscatter likelihood $\gamma$. Optionally, processor 860 outputs other data, such as remission images 125, in addition to sub-diffuse scattering parameters 132.

Without departing from the scope hereof, machine-readable instructions 820 may further include instructions for performing step 240 of method 200 (FIG. 2), in which case processor 860 may output information about the meso/micro-scale structure of material 140, which is derived from sub-diffuse scattering parameters 132. Processor 860 may output such information in combination with, or instead of, sub-diffuse scattering parameters 132.

Machine-readable instructions 820 form a software product that upon execution by a processor, such as processor 860, perform step 530 of method 500 and/or step 630 of method 600. Without departing from the scope hereof, machine-readable instructions 820 may be a stand-alone software product configured for installation on a third-party computer system to realize computer system 800.

Example I: Model Determination Through Monte Carlo Simulations

Example I discusses one example of method 700 (FIG. 7), wherein Monte Carlo simulations were used to determine $R_{d,model}(\mu'_s, \gamma, f_x)$ discussed above in reference to FIG. 5.

Example I utilized a customized version of a compute unified device architecture (CUDA) accelerated Monte Carlo (MC) code described by Calabro et al. in "*Improved empirical models for extraction of tissue optical properties from reflectance spectra*", Proc. SPIE 8230, 82300H (2012), which is incorporated by reference herein in its entirety. The model geometry, of the structured-light imaging system and material under investigation, was constructed to mimic a point-source incident on the air interface of a semi-infinite turbid medium with thickness of 100 centimeters (cm) and a maximal radial distance of 20 cm from the source location. The index of refraction of the medium and air were specified as medium n=1.37 and air n=1.0, respectively. Both source and detector were oriented normal to the medium/air interface with numerical apertures specified as NA=0.15. Photons that scattered within the medium and remitted across the medium/air interface within the cone of acceptance for the detector were collected. The simulation returned the radial distance $\rho$ between incidence and remission, which was discretely binned with a spacing of 0.1 millimeters (mm).

Simulations were performed over a wide range of scattering parameters. The modified Henyey-Greenstein form of the scattering phase function $P(\theta_s)$, wherein $\theta_s$ is the remission angle, was selected to allow independent modification of $g_1$ and $g_2$. Optical properties were specified to simulate a range of $\mu'_s$=[0.3, 0.5, 1, 3, 5, 10] mm$^{-1}$ for 18 unique phase combinations of $g_1$=[0.75, 0.85, 0.95] and $\gamma$=[1.3, 1.4, 1.5, 1.6, 1.7, 1.8, 1.9]; in each simulation $\mu_s$ was selected to return the appropriate $\mu'_s$ for a specified $g_1$. In all, 108 independent simulations were performed, each initializing 108 photons.

To convert the spatially resolved MC outputs of demodulated remission $R_d(\rho)$ to spatial-frequency resolved demodulated remission $R_d(f_x)$, a 1-D Hankel Transform was performed as described by Cuccia et al. in "Quantitation and mapping of tissue optical properties using modulated imaging", J. Biomed. Opt. 14(2), 024012 (2009), which is incorporated by reference herein in its entirety:

$$R_d(f_x) = \sum_{i=1}^{n} \rho_i J_0(f_x \rho_i) R_d(\rho_i) \Delta \rho_i,$$

wherein $J_0(f_x \rho_i)$ is the zeroth-order Bessel function of the first kind. This transformation was used to estimate $R_d(f_x)$ for 50 spatial frequencies over the range [0-2.0] mm$^{-1}$, and $R_d(f_x)$ was applied to all MC simulated measurements to yield 5400 combinations of $\mu'_s$, $\gamma$, and $f_x$.

Figure 9:
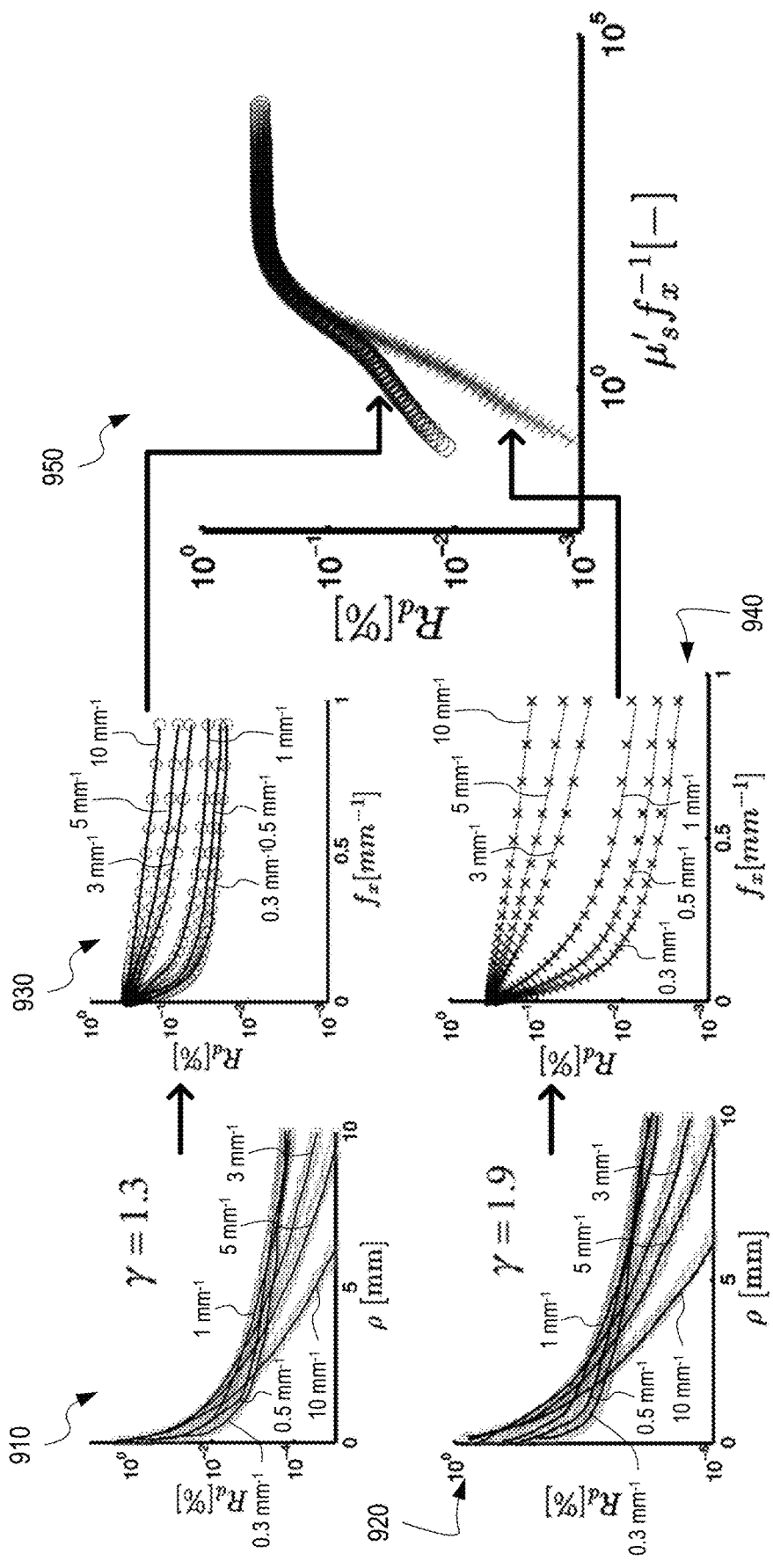
FIG. 9 shows results of Monte Carlo simulations used to determine an example of the model of FIG. 7.

FIG. 9 shows exemplary results of the MC simulations. Plot 910 shows $R_d(\rho)$ for $\gamma=1.3$ and $\mu'_s=[0.3, 0.4, 1, 3, 5, 10]$ mm$^{-1}$. Plot 920 shows $R_d(\rho)$ for $\gamma=1.9$ and $\mu'_s=[0.3, 0.4, 1, 3, 5, 10]$ mm$^{-1}$. Plots 910 and 920 show that $R_d(\rho)$ exhibit an exponential decay in intensity as the distance $\rho$ increases, with the rates of decay dependent on $\mu'_s$.

Plot 930 shows $R_d(f_x)$ obtained by applying the 1-D Hankel transform to $R_d(\rho)$ of plot 910. Likewise, plot 940 shows $R_d(f_x)$ obtained by applying the 1-D Hankel transform to $R_d(\rho)$ of plot 920. The $R_d(f_x)$ data of plots 930 and 940 suggest two distinct trends: (a) $R_d(f_x)$ increases in response to increases in $\mu'_s$, and (b) $R_d(f_x)$ increases in response to decreases in $f_x$. Closer inspection reveals a coupled dependence of $R_d(f_x)$ on $\mu'_s$ and $f_x$, with a 10-fold increase in $\mu'_s$ from 0.5 to 5 mm$^{-1}$ at constant $f_x=0.1$ mm$^{-1}$ yielding a 6-fold increase in $R_d(f_x)$; the same change in remission is introduced by a 10-fold decrease in $f_x$ from 0.05 to 0.5 mm$^{-1}$ at constant $\mu'_s=1.0$ mm-1.

Plot 950 expresses $R_d(f_x)$ as a function of dimensionless scattering $\mu'_s f_x^{-1}$. Plot 950 is an exemplary outcome of step 710 of method 700. Plot 950 indicates how $\mu'_s$ and $f_x$ interchangeably affect $R_d(f_x)$. The dimensionless representation of the data in plot 950 also shows distinct transport regimes that depend on the magnitude of $\mu'_s f_x^{-1}$. For high values of $\mu'_s f_x^{-1}$ (i.e., greater than 10), $R_d(f_x)$ is insensitive to $P(\theta_s)$ with no observable differences in $R_d(f_x)$ for different $\gamma$. The rationale for this observation is that these photons have experienced many scattering events and are insensitive to the direction of any individual scattering event. For low $\mu'_s f_x^{-1}$ values (i.e. less than 10), $R_d(f_x)$ has a $\gamma$-dependent slope vs. $\mu'_s f_x^{-1}$. Here, phase functions that specify a higher probability of backscatter yield higher remitted reflectance intensity for the same dimensionless scattering value. For example, at $\mu'_s f_x^{-1}=1$, $R_d(f_x)$ experiences a 4-fold increase between $\gamma=1.9$ and $\gamma=1.3$. These data provide an example of the profound influence that both $\mu'_s$ and $\gamma$ have on remittance sampled in the sub-diffuse transport regime.

Figure 10:
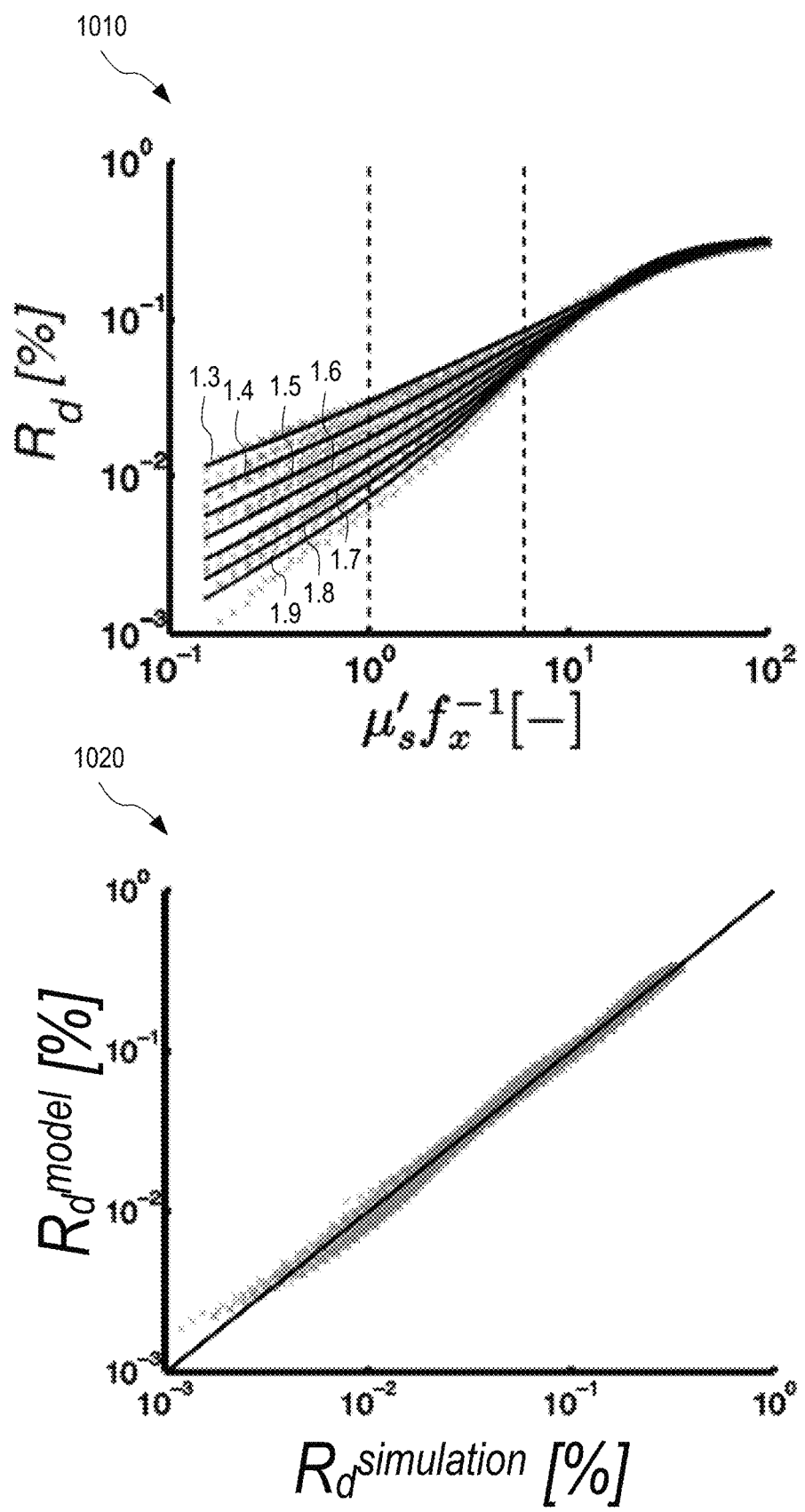
FIG. 10 shows results of fitting an empirical model to the simulation results of FIG. 9 to determine an example of the model of FIG. 7.

FIG. 10 shows exemplary results of fitting an empirical model to the simulation results of plot 950 of FIG. 9, as well as other results obtained together with the results of plot 950. The MC simulation associated with FIG. 9 returned $R_d(f_x)$ for $\mu'_s=[0.3-10]$ mm$^{-1}$, $g_1=[0.75-0.95]$, $\gamma=[1.3-1.9]$ and $f_x=[0-1]$ mm$^{-1}$. $R_{d,model}(\mu'_s, \gamma, f_x)$, discussed above in reference to FIG. 5, was fit to these results.

Plot 1010 shows both simulated data points (symbols) and model predictions (black lines) vs. $\mu'_s f_x^{-1}$ for $\gamma=[1.3-1.9]$. The model captures the important dynamics of the $R_d(f_x)$ vs. $\mu'_s f_x^{-1}$ relationship, including a $\gamma$-dependent slope for low $\mu'_s f_x^{-1}$, and a saturating $\gamma$-independent value at high $\mu'_s f_x^{-1}$. These model fits were obtained by estimating the fitting parameters of $R_{d,model}(\mu'_s, \gamma, f_x)$ as $\eta=0.003\pm1.1e^{-5}$, $\zeta_1=68.6\pm3.3$, $\zeta_2=0.98\pm0.01$, $\zeta_3=0.61\pm0.01$, and $\zeta_4=16.6\pm0.94$. The confidence intervals for the fitted parameters are small compared to their respective estimates, confirming the appropriateness of the selected parameter set.

Plot 1020 shows the model estimates of $R_d(f_x)$ vs. MC simulated $R_d(f_x)$. The estimates of $R_{d,model}(\mu'_s, \gamma, f_x)$, resulting from the fits shown in plot 1010, showed high quality fits to $R_d(f_x)$ from the MC simulations, over multiple orders of magnitude, with a mean residual of $\epsilon<6\%$ and a Pearson Correlation coefficient of 0.998. Plot 1020 is an exemplary outcome of step 720 of method 700.

Using the data of FIG. 10, it is possible to estimate the error that would be introduced into a prior-art SFDI measurement for a turbid medium without prior knowledge of the phase function $P(\theta_s)$. Assuming measurements of a purely scattering medium with $\mu'_s=1$ mm$^{-1}$ with $f_x=0.33$ mm$^{-1}$ would correspond to $\mu'_s f_x^{-1}=3$, a dimensionless scattering value that shows substantial sensitivity to $P(\theta_s)$ can be found with a 42% variation about the median $R_d$ for $\gamma$ in the range [1.3-1.9]. Sampling the same medium at a lower maximum spatial frequency $f_x=0.15$ mm$^{-1}$ would correspond to $\mu'_s f_x^{-1}=6.7$ and reduce the $\gamma$-associated variability in $R_d$ to 20%. This calculation considers a wide range of $\gamma$-values, and the $\gamma$-based distortions in biological tissue are likely to be less than these limits. These data support the concept that with proper selection of $f_x$, analysis using diffusion theory is appropriate. The data also show the substantial influence that $P(\theta_s)$ has on $R_d$ sampled above these limits. In the low dimensionless scattering region ($\mu'_s f_x^{-1}<6$), the demodulated remission can become dominated by the sub-diffuse signal, and substantial variations in remission intensity can be caused by either changes in the number of scatters or changes in the scattering phase function. For example, at $\mu'_s f_x^{-1}=1$, a 4-fold difference in $R_d$ is observed between $\gamma=1.3$ and $\gamma=1.9$. This difference in $R_d$ equates to a change in $\mu'_s f_x^{-1}$ by a factor of 4 for $\gamma=1.9$, or conversely, a change in $\mu'_s f_x^{-1}$ by a factor of 11 for $\gamma=1.3$. Thus, these data suggest that diffuse analysis of SFDI may require careful selection of $f_x$, especially in weakly-scattering media in order to avoid $\gamma$-based errors in $\mu'_s$ obtained by diffusion theory.

Example II: Model Inversion of $R_d$ ($\lambda$, $f_x$) to Estimate $\mu'_s$ ($\lambda$) and $\gamma(\lambda)$ for Simulated Measurements In Example II, the forward-model $R_{d,model}(\mu'_s, \gamma, f_x)$ determined in Example I, was used in an inversion algorithm to extract estimates of $\mu'_s(\lambda)$ and $\gamma(\lambda)$ from simulated measurements of $R_d$ ($\lambda$, $f_x$) sampled at multiple $f_x$.

Figure 11:
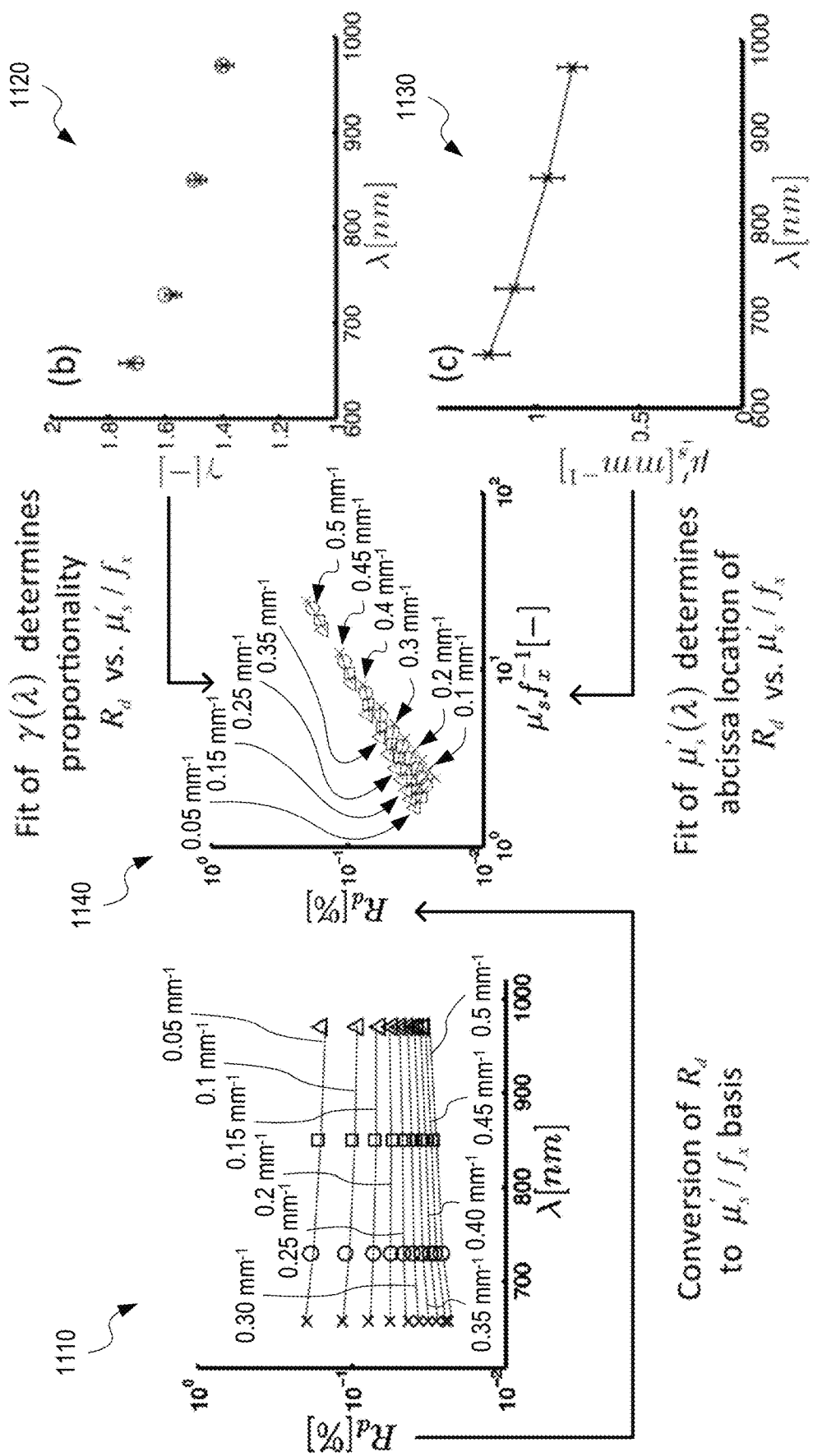
FIG. 11 illustrates inversion of the model of FIG. 10 to determine sub-diffuse scattering parameters.

FIG. 11 shows an example of these results within a simulated optical phantom with $R_d(\lambda, f_x)$ assembled from the Monte Carlo data of Example I (with 3% noise added). This example phantom specifies $\mu'_s(\lambda)=(\lambda/800)^{-1}$ in units of mm, and a wavelength-dependent decrease in $\gamma(\lambda)$ in the range [1.7-1.4], the spectral profiles of which are displayed in plots 1120 and 1130, respectively. Plot 1110 displays $R_d(\lambda, f_x)$ where marker shapes define each $\lambda=[658-970]$ nanometers (nm) and each data set, indicated by a solid line connecting a set of markers, indicate the sampled $f_x=[0.05-0.5]$ mm$^{-1}$. These data suggest that the wavelength-dependent remission slope is different for different $f_x$ values. Plot 1140 shows the $R_d(\lambda, f_x)$ vs. $\mu'_s f_x^{-1}$ relationship with a wavelength-dependent slope that depends on $\gamma(\lambda)$. The annotations in FIG. 11 reveal the interconnected flow of information within the fitting procedure for $R_d(\lambda, f_x)$, which interprets both the $\lambda$-dependent differences at each sampled $f_x$, and $\mu'_s f_x^{-1}$-dependent differences at each sampled $\lambda$. Simultaneous fitting of the $R_d(\lambda, f_x)$ data in plot 1110 accurately recovers $\mu'_s(\lambda)$ ($\varepsilon$<2%) and $\gamma(\lambda)$($\varepsilon$<1%) over the sampled wavelength range. These results provide the theoretical proof that $R_d(\lambda, f_x)$ sampled at multiple $f_x$ can be used to break the similarity relationship between $\mu'_s(\lambda)$ and $\gamma(\lambda)$.

Figure 12:
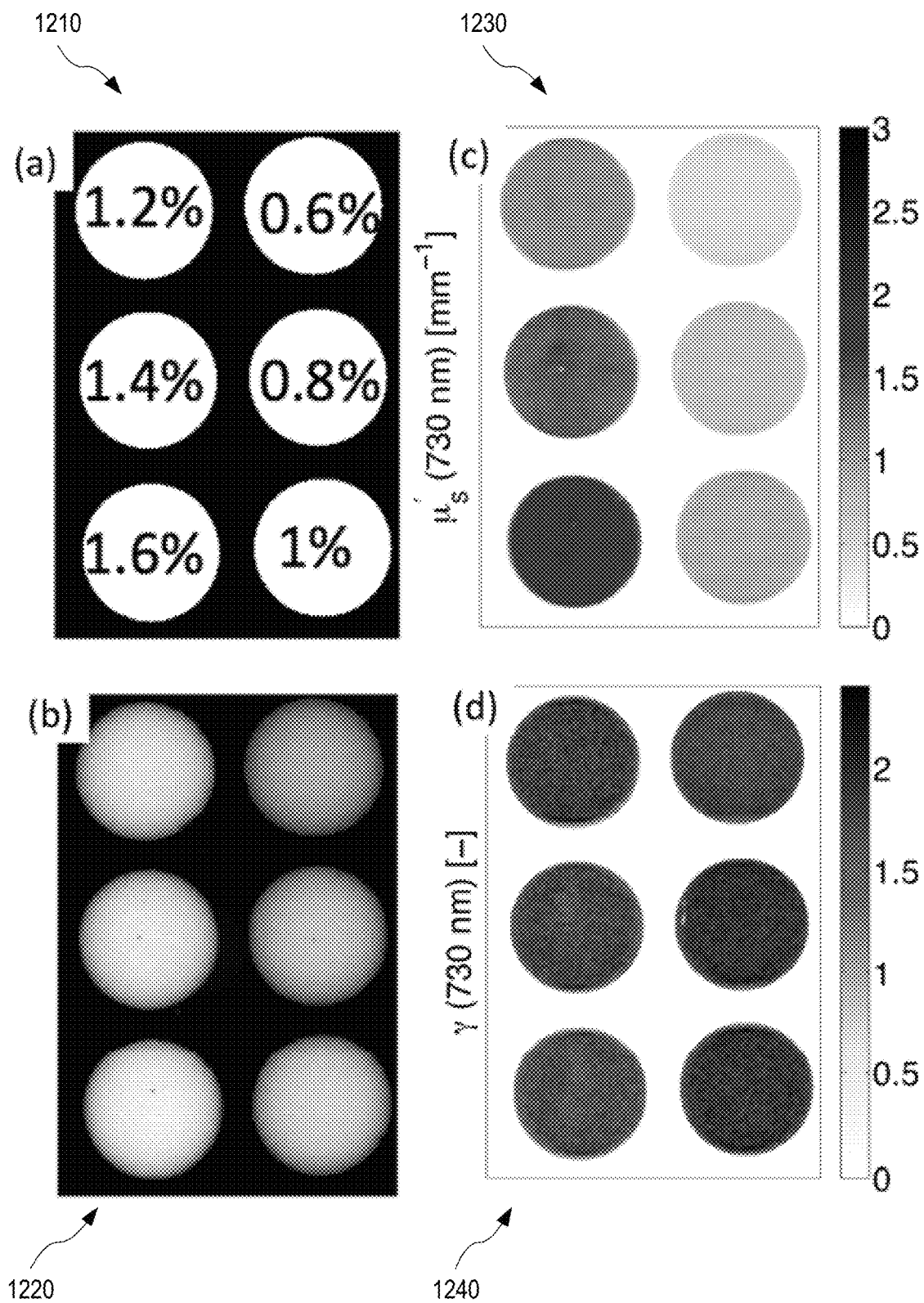
FIG. 12 shows results of structured-light imaging of optical phantoms, according to an embodiment.

Example III: Experimental Validation of Sub-Diffuse Scattering Imaging in Optical Phantoms FIG. 12 shows results of structured-light imaging of optical phantoms according to an embodiment of method 500 (FIG. 5) based upon $R_{d,model}(\mu'_s, \gamma, f_x)$ discussed in reference to FIG. 5. The results of FIG. 12 were obtained using an embodiment of structured-light imaging system 400 (FIG. 4), based upon a commercially available structured-light imaging device (Modulated Imaging Inc., Irvine, Calif., USA). The structured-light illuminator was a projector with four light emitting diode (LED) light sources having spectral wavelengths centered about [658, 730, 850, 970] nm. The system sampled a range of $f_x$=[0-0.5] mm$^{-1}$ at intervals of 0.05 mm$^{-1}$; higher $f_x$ values were observed to fall below the noise floor. Collection of specular reflection from the surface of the sample (an example of material 140) was limited by the use of cross-polarizers and orienting the source projector at an angle relative to the detector. The structured-light illumination patterns were sinusoids with spatial phase shifts $\phi$=[0, 2$\pi$3, 4$\pi$/3], as discussed in reference to FIG. 5.

Liquid phantoms were prepared by diluting amounts of Intralipid 20% (Frenius-Kabi, Bad Homburg, Germany) with phosphate buffered saline. Phantoms were prepared in volumes of 7 milliliters (mL) with dilutions yielding lipid percentages in the set: [0.6, 0.8, 1.0, 1.2, 1.4, 1.6] %. This dilution set produced $\mu'_s$=[0.4-1.8] mm$^{-1}$ and $\gamma$=[1.4-1.75] in the [658-970] nm wavelength range. Structured light images were acquired with the phantoms arranged on a black tray where the diameter of each sampled phantom was 25 mm within the full field of view [140 mm×114 mm]. Images were generated for all phantoms in a single field of view with an exposure time that was automatically adjusted for each sampled wavelength, and each intensity was corrected for differences in exposure time. Images of phantoms were analyzed using $R_{d,model}(\mu'_s, \gamma, f_x)$, fit to Monte Carlo simulations as discussed in Example I, were selected to mimic phase functions observed in Intralipid (i.e. four phase functions with $g_1$=[0.4, 0.6, 0.5, 0.7] and $\gamma$=[1.4, 1.5, 1.6, 1.7]). Images were thresholded to identify regions of the liquid phantoms from the black background. Model fitting was performed using $R_{d,model}(\mu'_s, \gamma, f_x)$ to estimate $\mu'_s(\lambda)$ and $\gamma(\lambda)$ on a pixel-by-pixel basis.

Diagram 1210 shows lipid percentages of Intralipid-based optical phantoms sampled in Example III. Image 1220 presents a corresponding wide-field monochromatic remission image (an example of remission image for $f_x$=0.05 mm$^{-1}$ and $\lambda$=730 nm) having increased remission intensity associated with increased lipid percentage. Map 1230 is a map of $\mu'_s$ (730 nm) estimates, obtained according to an embodiment of method 500, in the imaged phantoms. These data show proportionality between $\mu'_s$ and the lipid percentage, which is expected because an increase in the lipid volume fraction increases the number of scatterers within the turbid medium, and in turn the remitted reflectance. Map 1240 is a map of $\gamma$ (730 nm) estimates, obtained according to an embodiment of method 500, in each of the phantoms. Because $\gamma$ is an implicit scattering parameter, the true value of $\gamma$ is unchanged between the different volume fractions of lipid, with $\gamma$ (730 nm)=1.65 in all phantoms within the image. The model estimates accurately predict this invariance with the average in the six phantoms yielding $\gamma$ (730 nm)=1.69±0.1.

Figure 13:
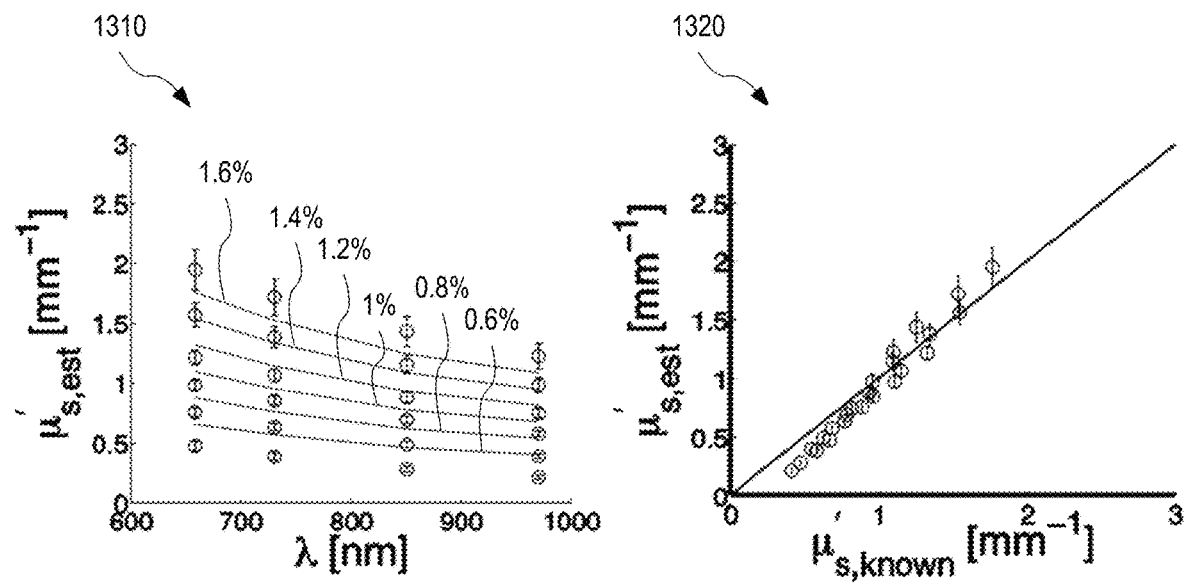
FIG. 13 shows reduced scattering coefficient results associated with FIG. 12.

FIG. 13 shows $\mu'_s(\lambda)$ results associated with the data of FIG. 12. Plot 1310 shows $\mu'_s(\lambda)$ spectra for both model-estimated (symbols) and known (lines) values; these spectra were evaluated from $R_d$ ($\lambda$, $f_x$) remission at the center of each imaged phantom. Plot 1320 suggests that good agreement exists between estimated and known $\mu'_s(\lambda)$ over the full range of $\mu'_s$=[0.4-1.8] mm$^{-1}$ with $\varepsilon$<16%; the black line with a slope of unity is included for visualization of the quality of the linear relationship.

Figure 14:
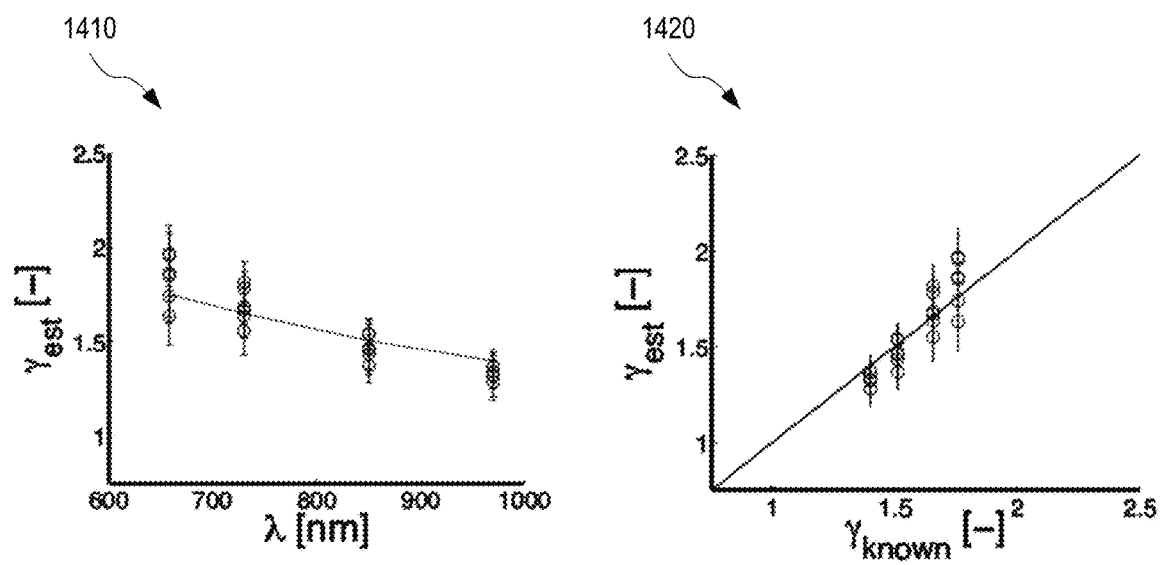
FIG. 14 shows backscatter likelihood results associated with FIG. 12.

FIG. 14 shows $\gamma(\lambda)$ results associated with the data of FIG. 12. Plot 1310 shows $\gamma(\lambda)$ spectra for both model-estimated (symbols) and known (lines) values. Plot 1320 indicates good agreement between model-estimated and known values over the measured wavelength range with $\varepsilon$<6%.

The data of FIGS. 12-14 validate the ability of model-based analysis of structured light to image spectral-variations accurately in sub-diffuse scattering parameters within a wide field of view.

Example IV: In Vivo Imaging of Superficial Scar

In Example IV, structured-light imaging was performed on a healthy human subject who had a superficial scar. The structured-light imaging and analysis was performed according to an embodiment of method 500 (FIG. 5) based upon $R_{d,model}(\mu'_s, \gamma, f_x)$ discussed in reference to FIG. 5. The results were obtained using an embodiment of structured-light imaging system 400 (FIG. 4), similar to the embodiment used in Example III.

Figure 15:
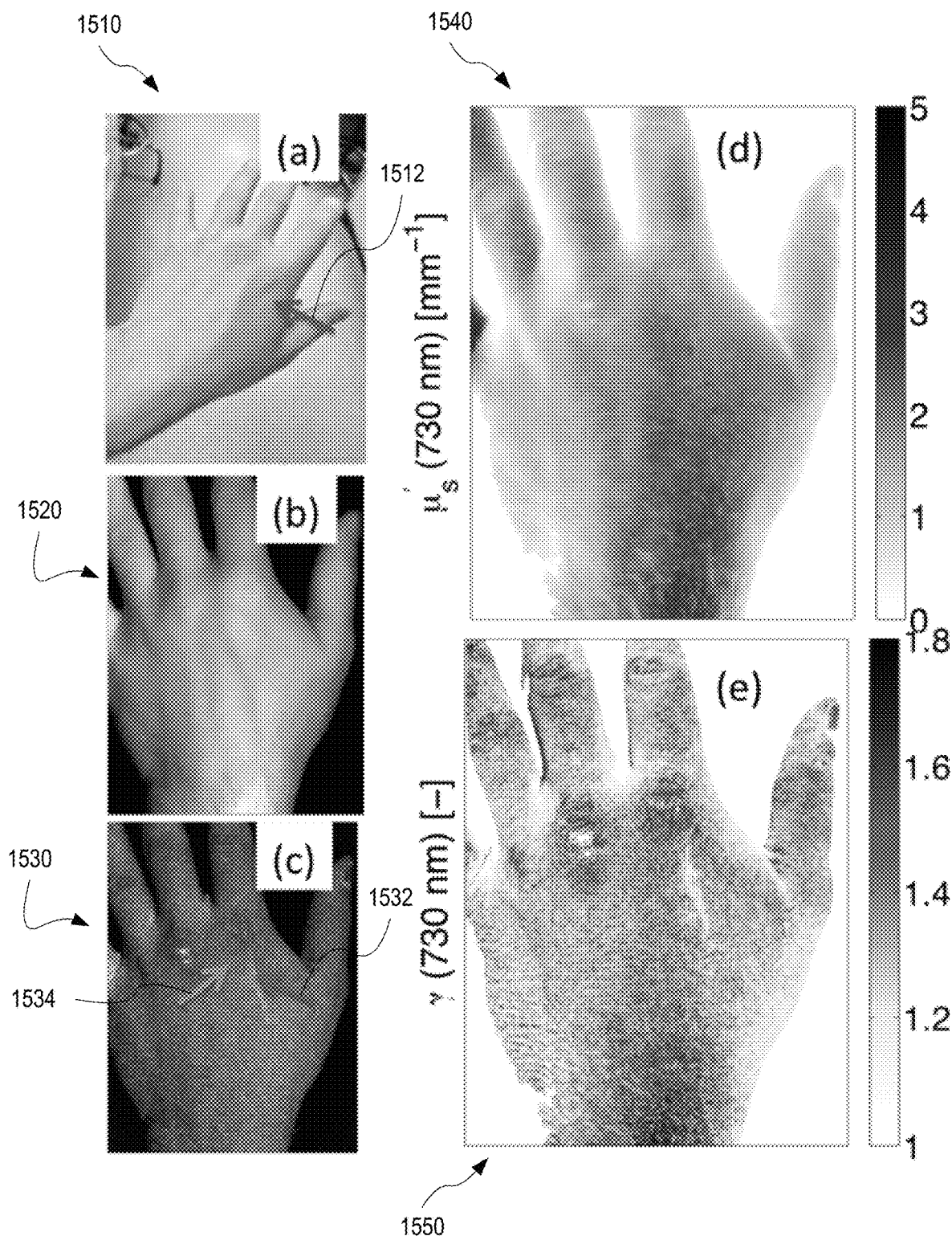
FIG. 15 shows structured-light imaging results for a superficial scar of a human subject.

FIG. 15 shows the left hand of the human subject together with structured-light imaging results. Image 1510 is a color image of the left hand, with arrow 1512 indicating the location of the scar located on the posterior side of the left hand near the distal end of the second metacarpal bone. Images 1520 and 1530 are demodulated remission intensity images. Image 1520 is obtained in the diffuse regime with $f_x$=0.05 mm$^{-1}$, and image 1530 is obtained in the sub-diffuse regime with $f_x$=0.5 mm$^{-1}$. Image 1530 distinguishes the scar as a bright area of contrast. This contrast is absent in image 1520. Maps 1540 and 1550 are spatial maps of $\mu'_s$ and $\gamma$, respectively, at 730 nm.

Figure 16:
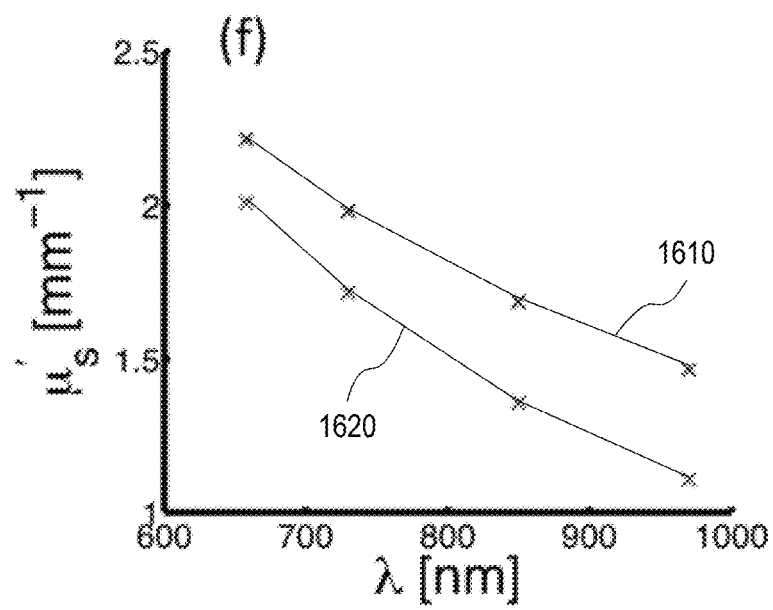
FIG. 16 shows reduced scattering coefficient results associated with FIG. 15.
Figure 17:
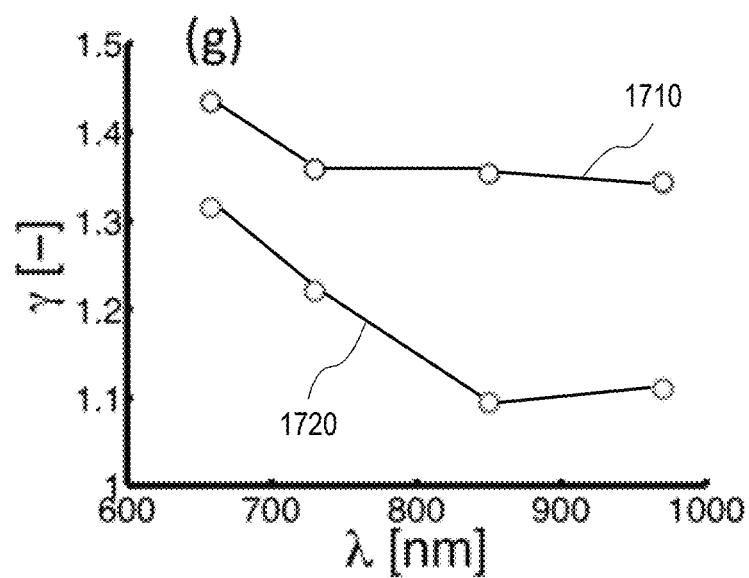
FIG. 17 shows backscatter likelihood results associated with FIG. 15.

FIG. 16 shows $\mu'_s(\lambda)$ for normal tissue (1610) at the position indicated by arrow 1534 in FIG. 15, and for the scar (1620) at the position indicated by arrow 1532 in FIG. 15. FIG. 17 shows $\gamma(\lambda)$ for normal tissue (1710) at the position indicated by arrow 1534 in FIG. 15, and for the scar (1720) at the position indicated by arrow 1532 in FIG. 15.

The map of $\mu'_s$ (see map 1540 of FIG. 15, and FIG. 16) does not provide obvious contrast between the superficial scar and surrounding normal tissue. However, substantial contrast is observed in $\gamma$ (see map 1550 of FIG. 15, and FIG. 17) between normal and scar tissue both in the spatial map and spectral profiles, with a maximum difference of 25% at 850 nm. These data suggest that imaging of sub-diffuse scattering parameters may provide endogenous contrast to differentiate between tissue types, even when tissues appear similarly under diffuse optical sampling.

Example V: Empirical Sub-Diffuse Scattering Parameters

Example V discusses embodiments of structured-light imaging system 100 (FIG. 1) and structured-light imaging method 200 (FIG. 2) used to determine sub-diffuse scattering parameters 132 that are empirical, i.e., non-model based.

Figure 18:
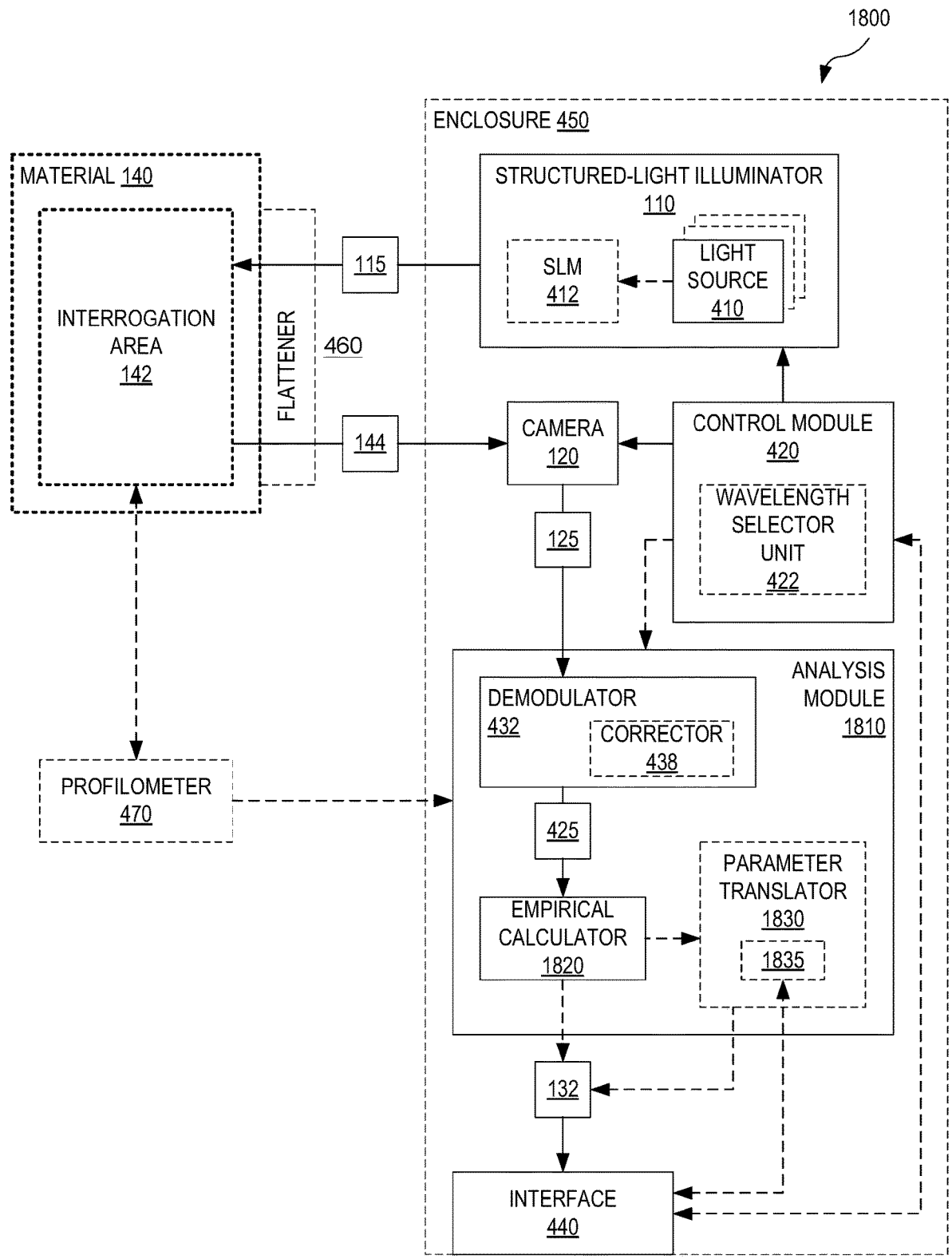
FIG. 18 illustrates a structured-light imaging system for determining empirical sub-diffuse scattering parameters, according to an embodiment.

FIG. 18 illustrates one exemplary structured-light imaging system 1800 for determining empirical sub-diffuse scattering parameters. Structured-light imaging system 1800 is an embodiment of structured-light imaging system 100 (FIG. 1).

Structured-light imaging system 1800 is similar to structured-light imaging system 400 (FIG. 4), except that analysis module 430 is replaced by an analysis module 1810. Analysis module 1810 is similar to analysis module 430, except for the following changes. Optimizer 436 is replaced by an empirical calculator 1820 and, optionally, a parameter translator 1830. Model 434 is replaced by an optional lookup table 1835 implemented in parameter translator 1830.

Empirical calculator 1820 determines empirical sub-diffuse scattering parameters from demodulated remission images 425. Exemplary empirical sub-diffuse scattering parameters include demodulated remission intensity, demodulated remission intensity as a function of spatial frequency $f_x$, slope of demodulated remission intensity as a function of spatial frequency $f_x$.

In one example, empirical calculator 1820 processes demodulated remission images 425 to determine spatially dependent demodulated remission as a function of spatial frequency $f_x$. Empirical calculator 1820 then determines (a) a spatially dependent absolute value of the demodulated remission intensity at a certain spatial frequency $f_x$, and (b) a spatially dependent slope of the demodulated remission intensity within a certain range of spatial frequencies $f_x$.

Optional parameter translator 1830 translates empirical sub-diffuse scattering parameters, determined by empirical calculator 1820, into model-based sub-diffuse scattering parameters such as the reduced scattering coefficient $\mu'_s$ and the backscatter likelihood $\gamma$, or directly into a tissue-type characterization. To perform this translation, parameter translator 1830 utilizes lookup table 1835 which provides model-based sub-diffuse scattering parameters, or tissue type, as a function of empirical sub-diffuse scattering parameters. Lookup table 1835 is, for example, based upon data similar to the data shown in plot 1010 (FIG. 10) and discussed in reference to Example I. Optional parameter translator 1830 may receive and/or output at least portions of lookup table 1835 via interface 440.

Analysis module 1810 outputs sub-diffuse scattering parameters 132 as empirical sub-diffuse scattering parameters determined by empirical calculator 1820, model-based sub-diffuse scattering parameters derived from the empirical sub-diffuse scattering parameters by parameter translator 1830, and/or tissue type characterization derived from the empirical sub-diffuse scattering parameters by parameter translator 1830.

Figure 19:
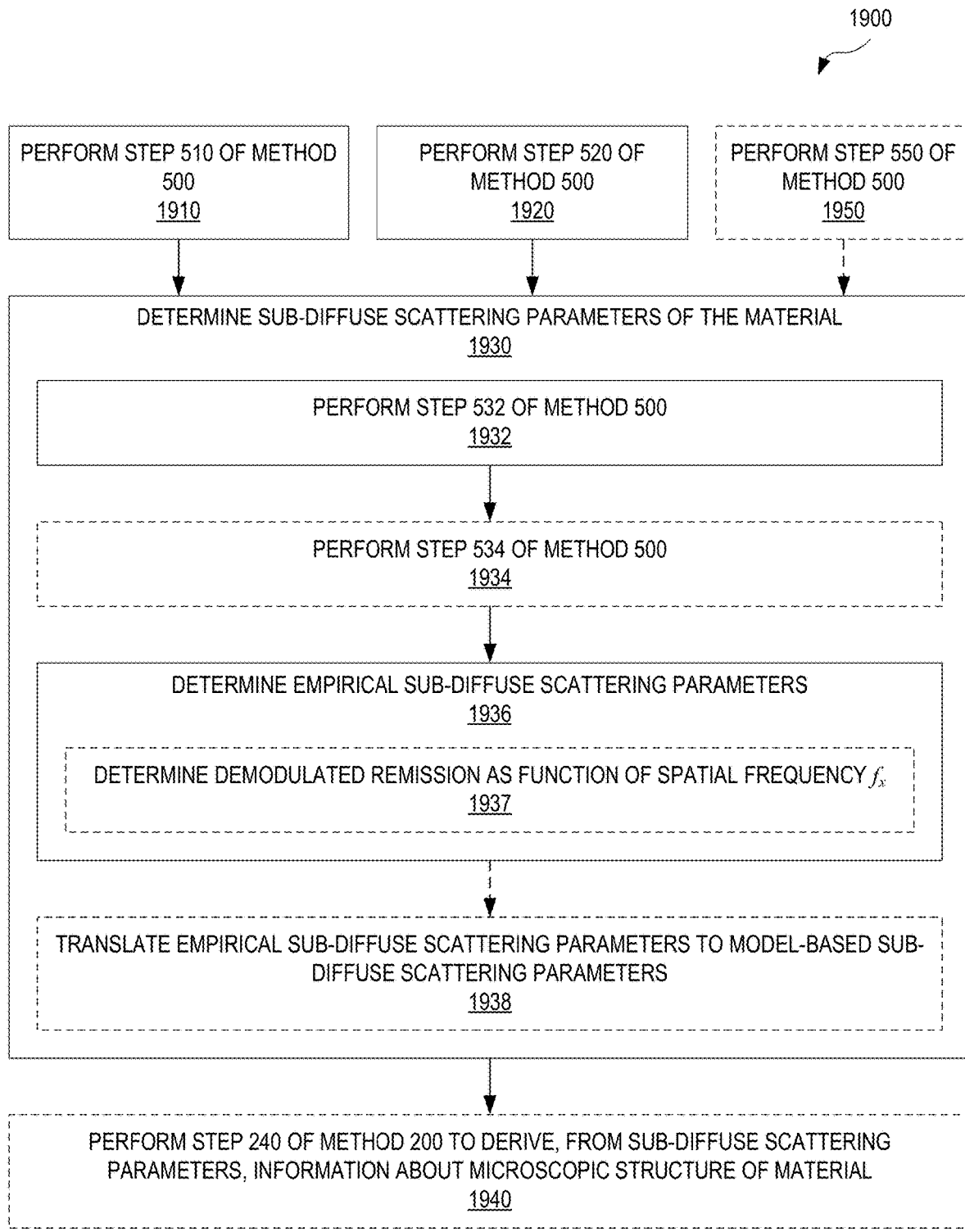
FIG. 19 illustrates a structured-light imaging method for determining empirical sub-diffuse scattering parameters, according to an embodiment.

FIG. 19 illustrates one exemplary structured-light imaging method 1900 for determining empirical sub-diffuse scattering parameters. Structured-light imaging method 1900 is an embodiment of structured-light imaging method 200 (FIG. 2), which is similar to structured-light imaging method 500 (FIG. 5).

In steps 1910 and 1920, method 1900 performs steps 510 and 520 of method 500, respectively, as discussed in reference to FIG. 5. In one example, structured-light imaging system 1800 performs steps 1910 and 1920, as discussed in reference to FIG. 5.

In a step 1930, method 1900 determines sub-diffuse scattering parameters of the material interrogated in steps 1910 and 1920. Step 1930 is similar to step 530 of method 500.

In a step 1932, method 1900 performs step 532 of method 500 to generate demodulated images 425, as discussed in reference to FIG. 5. In one example of step 1932, demodulator 432 of structured-light imaging system 1800 determines demodulated images 425, as discussed in reference to FIG. 5.

In a step 1936, method 1900 determines empirical sub-diffuse scattering parameters from demodulated remission images 425 determined in step 1932. In one example of step 1936, empirical calculator 1820 determines empirical sub-diffuse scattering parameters as discussed in reference to FIG. 18. In an embodiment, step 1936 includes a step 1937 of determining demodulated remission as a function of spatial frequency $f_x$, and deriving the empirical sub-diffuse scattering parameters from the demodulated remission as a function of spatial frequency $f_x$. In one example of step 1936, empirical calculator determines demodulated remission as a function of spatial frequency $f_x$, and related empirical sub-diffuse scattering parameters, as discussed in reference to FIG. 18.

In certain embodiments, step 1930 further includes a step 1938, that translates empirical sub-diffuse scattering parameters, determined in step 1936, to model-based sub-diffuse scattering parameters such as the reduced scattering coefficient $\mu'_s$ and the backscatter likelihood $\gamma$. In one example of step 1938, parameter translator 1830 translates empirical sub-diffuse scattering parameters, received from empirical calculator 1820, into model-based sub-diffuse scattering parameters, as discussed in reference to FIG. 18.

Optionally, method 1900 implements steps 534 and 550 as steps 1934 and 1950, respectively, to correct demodulated remission images 425 for spatial non-uniformity, as discussed in reference to FIG. 5.

In an embodiment, method 1900 includes a step 1940 that performs step 240 of method 200 to derive, from empirical and/or model-based sub-diffuse scattering parameters determined in step 1930, information about the meso/micro-scale structure of the interrogated material. Step 1940 may be performed by analysis module 1810, another computer system communicatively coupled with analysis module 1810, and/or by a human operator. In one example of step 1940, parameter translator 1830 translates the empirical sub-diffuse scattering parameters to tissue-type characterization using lookup table 1835.

Method 1900 may be extended to multiple spectral wavelengths in a fashion similar to the extension of method 500 to method 600 (FIG. 6).

Figure 20:
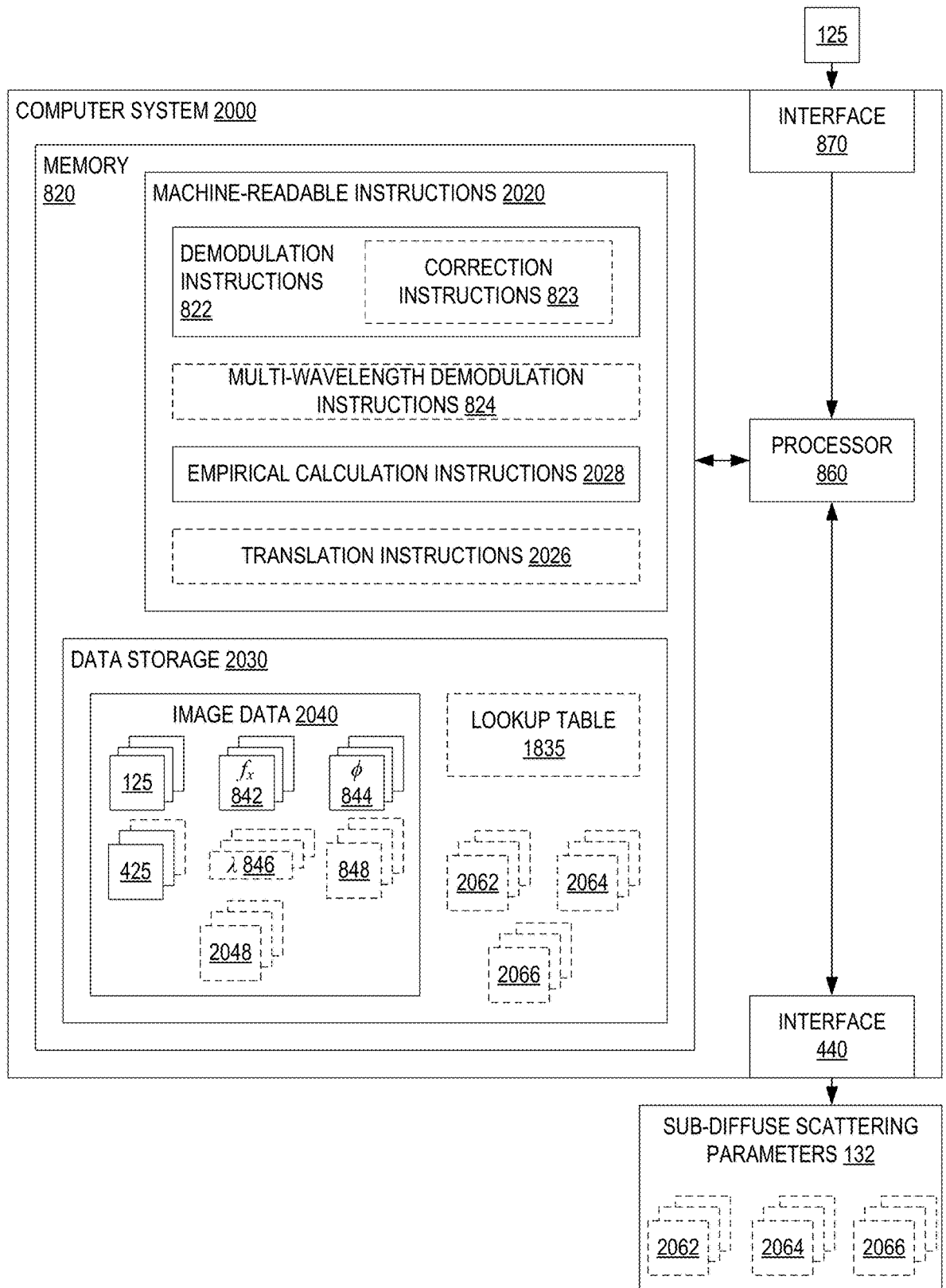
FIG. 20 illustrates a computer system for processing structured-light remission images to determine empirical sub-diffuse scattering parameters, according to an embodiment.

FIG. 20 illustrates one exemplary computer system 2000 that implements step 1930 of structured-light imaging method 1900 (FIG. 19), and/or implements a multi-spectral-wavelength extension of step 1930. Computer system 2000 is an embodiment of analysis module 1810 of structured-light imaging system 1800 (FIG. 18).

Computer system 2000 is similar to computer system 800 (FIG. 8), except that memory 820 is implemented with machine-readable instructions 2020 (instead of machine-readable instructions 820) and data storage 2030 (instead of data storage 830).

Machine-readable instructions 2020 is similar to machine-readable instructions 820, except that optimization instructions 828 and model 826 are replaced by empirical calculation instructions 2028 and optional translation instructions 2026. Upon execution by processor 860, empirical calculation instructions 2028 performs the functions of empirical calculator 1820. Upon execution by processor 860, translation instructions 2026 performs the functions of parameter translator 1830.

Data storage 2030 includes at least one of (a) empirical sub-diffuse scattering parameter(s) 2062 determined using empirical calculation instructions 2028, (b) model-based sub-diffuse scattering parameter(s) 2064 determined using translation instructions 2026, and (c) tissue-type characterization(s) 2066 determined using translation instructions 2026. Data storage 2030 further includes an image data storage 2040 that is similar to image data storage 840. As compared to image data storage 840, image data storage 2040 may further include one or more spatial maps 2048 of sub-diffuse scattering parameters determined using machine-readable instructions 2020. In addition, data storage 2030 may include lookup table 1835. Processor 860 may retrieve data from lookup table 1835 when executing translation instructions 2026.

In computer system 2000, interface 440 outputs sub-diffuse scattering parameters 132 as empirical sub-diffuse scattering parameter(s) 2062, model-based sub-diffuse scattering parameter(s) 2064, and/or tissue-characterization(s) 2066, optionally in the form of spatial map(s) 2048.

Example VI: Ex Vivo Imaging of Breast Tissue

In Example VI, structured-light imaging was performed ex-vivo on breast tissue. Example VI demonstrates differentiation of tissue morphologies based sub-diffuse scattering parameter maps of surgically excised human breast tissue. The structured-light imaging and analysis was performed according to an embodiment of method 600 (FIG. 6) implementing step 632 and utilizing a reflectance model $R_{d,model,ext}(\mu'_s, \gamma, f_x)$ that is an extension of the sub-diffuse model $R_{d,model}(\mu'_s, \gamma, f_x)$ discussed in reference to FIG. 5. This extension $R_{d,model,ext}(\mu'_s, \gamma, f_x)$ includes (a) analyzing low spatial frequency data to determine estimates of the diffuse optical properties of reduced scattering coefficient $\mu'_s$ and absorption coefficient $\mu_a$, and (b) applying the sub-diffuse model $R_{d,model}(\mu'_s, \gamma, f_x)$ to analyze data of high spatial frequency data to yield the reduced scattering coefficient $\mu'_s$ and the backscattering parameter $\gamma$. Example VI assumes that the reduced scattering coefficient $\mu'_s$ depends on the spectral wavelengths $\lambda$ according to the power law $\mu'_s(\lambda)=a(\lambda/\lambda_0)^{-b}$ wherein $\lambda_0$ is a 800 nm, a is the scatter amplitude, b is the scatter slope. Example VI optimizes the backscatter likelihood $\gamma(\lambda)$ for each of the three spectral wavelengths. The results were obtained using an embodiment of structured-light imaging system 400 (FIG. 4), similar to the embodiment used in Example III but configured with three light emitting diode (LED) light sources having spectral wavelengths centered about 658, 730, and 850 nm, respectively.

Imaging was performed using a commercial spatial frequency domain system (Modulating Imaging, Inc., Irvine, Calif.). This unit acquired spatial frequencies over the range of $f_x=[0–0.2, 0.5–0.9]$ mm$^{-1}$ in steps of 0.05 mm$^{-1}$ for each source LED. In order to maximize signal from weakly scattered photons, cross-polarizing filters were removed from the commercial system. However, to mitigate the effect of specularly reflected photons, projections were obliquely illuminated and a signal acquired from a measurement of water in a deep ($\approx$50 cm) well with dark non-reflecting walls was subtracted from both the sample and reference intensity maps to approximate the specular reflection. Maps of calibrated reflectance were calculated by ratioing demodulated intensity maps of the sample with a reference measurement of Intralipid 1% and multiplying by a model reflectance value calculated from a sub-diffuse model $R_{d,model}(\mu'_s, \gamma, f_x)$ and $R_{Diff}(\mu'_s, \mu_a, f_x)$ using optical properties for Intralipid known in the art, wherein $$R_{Diff}(\mu'_s, \mu_a, f_x) = \frac{3\alpha' \frac{\mu'_s}{\mu_{tr}}}{\left(\frac{\sqrt{3\mu_a\mu_{tr}} + \frac{(2\pi f_x)^2}{\mu_{tr}}}{} + 1\right)\left(\frac{\sqrt{3\mu_a\mu_{tr}} + \frac{(2\pi f_x)^2}{\mu_{tr}}}{} + 3\alpha'\right)},$$

wherein $\mu_{tr}=\mu_a+\mu'_s$, and $\alpha'$ is a proportionality constant account for surface boundary effects. The reflectance model $R_{d,model,ext}(\mu'_s, \gamma, f_x)$ is defined as $$R_{d,model,ext}(\mu'_s, \gamma, f_x) = \begin{cases} R_{Diff}(\mu'_s, \mu_a, f_x) & \text{if } f_x \leq 0.2 \text{ mm}^{-1}, \\ R_{d,model}(\mu'_s, \gamma, f_x) & \text{if } f_x \geq 0.5 \text{ mm}^{-1}. \end{cases}$$

The reflectance model $R_{d,model,ext}(\mu'_s, \gamma, f_x)$ is thus broken into piecewise contributions from the semi-empirical sub-diffusive expression, according to $R_{d,model}(\mu'_s, \gamma, f_x)$ and a diffusion theory model according to $R_{Diff}(\mu'_s, \mu_a, f_x)$. The combination is complementary because the sub-diffusive model, $R_{d,model}(\mu'_s, \gamma, f_x)$, is sensitive to scatter directionality but does not account for optical absorption whereas the diffusion theory model, $R_{Diff}(\mu'_s, \mu_a, f_x)$, assumes diffusive photon propagation but characterizes both diffuse scatter and absorption. Thus, only spatial frequencies above 0.5 mm$^{-1}$, which have negligible signal contribution from absorption for typical optical properties of tissue in the near-infrared window, were analyzed with the sub-diffusive model, and spatial frequencies below 0.2 mm$^{-1}$, which meet assumptions of diffusion for typical tissue optical properties in the NIR window, were analyzed with the diffusion theory model. The calibrated images of demodulated reflectance $R_d(f_x, \lambda)$ over the acquired spatial frequencies and wavelengths were inverted into maps of $\mu_a$, $\mu'_s$, and $\gamma$ with a nonlinear least squares minimization using the expressions for $R_{Diff}(\mu'_s, \mu_a, f_x)$ and $R_{d,model}(\mu'_s, \gamma, f_x)$.

Optical scatter parameter maps of surgically excised human breast tissue were compared to spatially co-registered histopathologic diagnoses. Example VI included 22 breast tissue specimens from 17 patients undergoing elective and consented breast surgeries. After excision and margin inking, specimens were "bread loafed" according to standard-of-care protocol. Upon gross inspection of the loafed specimen, excess tissue not needed to make a pathologic diagnosis was evaluated. Specifically, excess tissue conforming to a standardized gross diagnosis of normal glandular, adipose, benign fibroadenoma, or invasive carcinoma (both lobular and ductal) was cut to a size of approximately 25 mm×25 mm×5 mm and immediately imaged. In total for each tissue type Example VI sampled: Adipose (3 patients, 3 specimens, 5785 pixels), Normal Glandular (8 patients, 10 specimens, 19391 pixels), Benign Fibroadenoma (3 patients, 4 specimens, 10459 pixels), and Invasive Carcinoma (5 patients, 5 specimens, 6984 pixels).

All tissue samples were imaged with structured light using structured-light imaging system 400. The imaging procedure had a duration of about 2 minutes. Additionally, a select set of specimens were also imaged with a dark-field reflectance microscope. Following optical imaging tissue samples underwent standard histological processing, including formalin fixation and H&E staining. Prepared tissue sections were evaluated by an expert pathologist, who outlined final diagnoses over digital scans of the entire section. These annotated digital histology sections were readily co-registered to the optical scattering maps with simple rigid transformations, and were used to create binary masks for pixel-based clustering analysis. Pixels near the boundary of the tissue were excluded from the clustering analysis. All of the breast specimens included in the clustering analysis were uniformly comprised of a single breast tissue type in order to capture differences between well-defined tissue morphologies. However, one localized invasive cancer surrounded by adipose and fibrous tissue was analyzed to demonstrate application of method to a heterogeneous tissue specimen.

Inspection of the microscopic imaging data revealed differences in microscopic morphology between tissue types. Adipose tissue was almost completely comprised of adipocytes with large lipid vacuoles on the size scale >25 µm, creating a tissue that is markedly forward-scattering having a low cross section with such large Mie scatterers. Normal glandular tissue appeared to be largely comprised of stromal collagen as shown by an overwhelming pink color in the H&E composite with some fat and also functional, organized, yet sparse cellularity appearing in the high magnification H&E. Although collagen fibers are relatively weak, Mie scatterers with a diameter of only a few µm, collagen fibrils (about 200 nm-300 nm) and their striations (<100 nm) are much smaller and strong Rayleigh scatters. A fibroadenoma was characterized by the benign proliferation of stromal collagen around the functional epithelium, which in turn compresses and expands the cellular epithelium. Invasive carcinoma was characterized by uncontrolled growth of the epithelium, with very high nuclear density and as well as an increase in the nuclear-to-cytoplasmic ratio and mitochondrial density. The size scale of both nuclei (about 5 µm) and mitochrondia (about 1 µm) characterized them as weak Mie scatterers.

Dark-field microscopy reflectance images from fresh tissue samples showed back-scattered light intensity from structural features. The dark-field images were acquired on a slightly larger length scale from the high-magnification H&E images discussed above. Dark field images provide a unique scatter-based contrast from thick tissue samples and showed clear differences in the micro-architecture of adipose with the more densely packed tissues. The effects of multiple scattering confound resolution of many of the ultrastructural features in the fresh, thick tissue sample that is provided by H&E analysis.

Example VI also obtained scanned composite sections of the histology, which provide a description of the relative distribution of structural features on the mm-cm length scale.

In addition, Example VI obtained white light photographs of each tissue type, with adipose tissue exhibiting a markedly yellow color, while the other more fibrous tissues appear as various shades of white and red. Quick inspection of these images showed differences between tissue samples. Adipose tissue had a pronounced high $\gamma$ and low scatter amplitude, which is consistent with large cells that dominate light transport as Mie (forward) scatterers. Conversely, normal glandular tissue presented a low $\gamma$ and a high scatter amplitude, which is associated with a denser tissue composed of fibrils and striations that contribute meaningfully to Rayleigh (backward) scattering. Comparative inspection of the parameter maps of fibroadenoma and invasive carcinoma with normal glandular tissue showed a reduced $\gamma$ and an increased scatter slope, suggestive of a relative increase in Mie scatterers. Additionally, both glandular tissue and invasive carcinoma showed increased scattering amplitudes compared with fibroadenoma, which is descriptive of the density of scattering structures within each tissue types.

Example VI utilized 3D cluster plots, with the axes indicating the scatter amplitude a, scatter slope b, and $\gamma$, respectively. Four distinct clusters appeared, despite noticeable overlap in the cluster visualization. A quantitative analysis of the cluster plots showed that differences in the distributions of $\gamma$ (658 nm) were statistically significant for all tissue type pairings, except for invasive carcinoma compared with fibroadenoma, which did not yield a significant difference in distributions for all scattering parameters; however, this lack of statistical significance may be due in-part to the small sample size used in Example VI.

To mimic a more clinically-relevant situation, Example VI also performed structured light imaging of tissue samples containing multiple tissue types, specifically freshly excised cancerous breast tissue with surrounding fat and normal fibrous tissue. The data demonstrated the ability to rapidly assess whole tissue specimens through sub-diffusive imaging, where point-source or microscopic-based tissue interrogation methods would have to randomly sample a large number of locations to achieve similar robustness. Moreover, these data motivate a sampling strategy that uses multiple length-scale imaging for evaluation of malignancy within clinical tissue samples; such an approach would use sub-diffuse imaging to return a wide-field map of microstructural parameters that may identify regions of interest, either for more detailed interrogation via microscopic imaging, or for guided selection of biopsy locations to obtain definitive histological confirmation.

Combinations of Features

Features described above as well as those claimed below may be combined in various ways without departing from the scope hereof. For example, it will be appreciated that aspects of one system, or method, for guiding tissue resection, described herein, may incorporate or swap features of another system, or method, for guiding tissue resection, described herein. The following examples illustrate some possible, non-limiting combinations of embodiments described above. It should be clear that many other changes and modifications may be made to the systems and methods herein without departing from the spirit and scope of this invention:

(A1) A method for determining sub-diffuse scattering parameters of a material may include (a) illuminating the material with structured light, (b) imaging remission by the material of the structured light, and (c) determining, from images capture in the step of imaging, sub-diffuse scattering parameters of the material.

(A2) In the method denoted as (A1), the step of determining may include quantitatively determining the sub-diffuse scattering parameters of the material.

(A3) In either or both of the methods denoted as (A1) and (A2), the sub-diffuse scattering parameters may include reduced scattering coefficient and backscatter likelihood.

(A4) In the method denoted as (A3), the step of determining may include producing a spatial map of the reduced scattering coefficient and the backscatter likelihood.

(A5) Either or both of the methods denoted as (A3) and (A4) may further include deriving, from the backscatter likelihood, information about microscopic structure of the material.

(A6) In any of the methods denoted as (A3) through (A5), the step of determining may include determining the backscatter likelihood as γ=(1−g2)/(1−g1), wherein g1 and g2 are first and second Legendre moments, respectively, of scattering phase function of the material.

(A7) In any of the methods denoted as (A3) through (A6), the step of illuminating may include, at a spectral wavelength of the structured light, temporally varying periodic structure of the structured light to produce different spatial frequencies and different spatial phase shifts, each of the spatial frequencies being associated with a plurality of the different spatial phase shifts, the step of imaging may include capturing a plurality of images including an image of the remission for each of the different spatial frequencies and for each of the different spatial phase shifts associated with each of the different spatial frequencies, and the step of determining may include processing the plurality of images to deduce wavelength-specific values of the reduced scattering coefficient and the backscatter likelihood.

(A8) In the method denoted as (A7), the plurality of different spatial phase shifts may be a first spatial phase shift ϕ1, a second spatial phase shift ϕ2=ϕ1+2π/3, and a third spatial phase shift ϕ3=ϕ1+4π/3.

(A9) In the method denoted as (A7), the plurality of different spatial phase shifts being at least three spatial phase shifts equidistantly spanning a full 2πc phase rotation.

(A10) In the method denoted as (A9), the plurality of different spatial phases may be N spatial phases ϕ=ϕ1, ϕ1+2π/N, . . . , ϕ1+(N−1)2π/N, wherein N is an integer greater than two, and φ1 is a constant phase.

(A11) In any of the methods denoted as (A7) through (A10), the different spatial frequencies may include (a) a lower spatial frequency sufficiently low that the remission associated therewith is sensitive to the reduced scattering coefficient, and (b) a higher spatial frequency sufficiently high that the remission associated therewith is sensitive to the backscatter likelihood.

(A12) In the method denoted as (A11), the different spatial frequencies may further include a spatial frequency of substantially zero to provide a measurement of absorption coefficient of the material.

(A13) In either or both of the methods denoted as (A11) and (A12), the lower spatial frequency may correspond to interrogation depth, of the material, associated at least in part with diffuse scattering, and the higher spatial frequency may correspond to interrogation depth, of the material, associated at least in part with sub-diffuse scattering.

(A14) In any of the methods denoted as (A11) through (A13), the higher spatial frequency may be greater than a third of the reduced scattering coefficient.

(A15) In any of the methods denoted as (A7) through (A14), the step of determining may include (a) generating demodulated images respectively associated with the different spatial frequencies, wherein each one of the demodulated images is generated from those of the plurality of images captured for a respective one of the different spatial frequencies, and (b) fitting a model for demodulated remission, sensitive to (i) the wavelength-specific values of the reduced scattering coefficient and the backscatter likelihood and (ii) spatial frequency of the periodic structure, to intensities in the demodulated images, to ascertain the wavelength-specific values of the reduced scattering coefficient and the backscatter likelihood.

(A16) The method denoted as (A15) may further include, after the step of generating demodulated images and before the step of fitting the model, correcting the intensities for spatial non-uniformity, apart from the periodic structure, introduced by one or both of (1) structured-light illuminator used to perform the step of illuminating and (2) camera used to perform the step of imaging.

(A17) In the method denoted as (A16), the step of correcting may include generating demodulated reference images, similar to the demodulated images, of remission from a reference reflector.

(A18) In any of the methods denoted as (A15) through (A17), the step of fitting may be performed independently for each of at least some of all spatial locations represented by the demodulated images, to produce a spatial map of the wavelength-specific values of the reduced scattering coefficient and the backscatter likelihood.

(A19) In the method denoted as (A18), in the step of fitting, each spatial location corresponding to a pixel location in the demodulated images.

(A20) In any of the methods denoted as (A15) through (A19), the step of fitting may include ascertaining the wavelength-specific value of the backscatter likelihood as γ=(1−g2)/(1−g1), wherein g1 and g2 are first and second Legendre moments, respectively, of scattering phase function of the material, wherein, in the step of fitting, the model specifies remission as a function of γ and product between (a) the wavelength-specific value of the reduced scattering coefficient and (b) spatial frequency of the structured light.

(A21) In the method denoted as (A20), in the step of fitting, the model may be $$R_d(\mu'_s, \gamma, f_x) = \eta\left(1 + (\zeta_4\gamma^{-2})(\mu'_s f_x^{-1})^{(-\zeta_3\gamma)}\right)\left[\frac{(\mu'_s f_x^{-1})^{(-\zeta_2\gamma)}}{\zeta_1\gamma^2 + (\mu'_s f_x^{-1})^{(-\zeta_2\gamma)}}\right],$$

wherein $R_d$ is the remission, $\mu'_s$ is the wavelength-specific value of the reduced scattering coefficient, $f_x$ is the spatial frequency of the structured light, $\eta$ is a predetermined constant, and each of $\zeta_i$, $i=1, 2, 3$, and 4, is a predetermined constant.

(A22) In the method denoted as (A21), the step of fitting may include fitting the model to the intensities using $\mu'_s$ and γ as fitting parameters.

(A23) Any of the methods denoted as (A7) through (A22) may include repeating the step of illuminating and the step of imaging for a plurality of spectral wavelengths, and the step of determining may include processing the plurality of images, associated with each of the plurality of spectral wavelengths, to deduce wavelength-specific values of the reduced scattering coefficient and the backscatter likelihood for each of the plurality of spectral wavelengths.

(A24) In the method denoted as (A23), the step of determining may include (a) for each of the plurality of spectral wavelengths, generating demodulated images respectively associated with the different spatial frequencies, each one of the demodulated images being generated from those of the plurality of images captured for a respective one of the different spatial frequencies, and (b) fitting a wavelength-dependent model for demodulated remission, sensitive to (i) the wavelength-specific values of the reduced scattering coefficient and the backscatter likelihood and (ii) spatial frequency of the periodic structure, to intensities in the demodulated images associated with all of the plurality of spectral wavelengths, to determine the wavelength-specific values of the reduced scattering coefficient and the backscatter likelihood for each of the plurality of spectral wavelengths.

(A25) In the method denoted as (A24), the step of fitting may include ascertaining, for each of the plurality of spectral wavelengths, the wavelength-specific value of the backscatter likelihood as $\gamma=(1-g2)/(1-g1)$, wherein g1 and g2 are first and second Legendre moments, respectively, of scattering phase function of the material, wherein, in the step of fitting, the model specifies remission as a function of $\gamma$ and product between (1) the wavelength-specific value of the reduced scattering coefficient and (2) spatial frequency of the structured light.

(A26) In the method denoted as (A25), in the step of fitting, the model may be $$R_d(\mu_s'(\lambda), \gamma(\lambda), f_x) =$$

$$\eta\left(1 + (\zeta_4(\gamma(\lambda))^{-2})(\mu_s'(\lambda)f_x^{-1})^{(-\zeta_3(\gamma))}\right) \times \left[\frac{(\mu_s'(\lambda)f_x^{-1})^{(-\zeta_2\gamma(\lambda))}}{\zeta_1(\gamma(\lambda))^2 + (\mu_s'(\lambda)f_x^{-1})^{(-\zeta_2\gamma(\lambda))}}\right],$$

wherein $R_d$ is the remission, is the spectral wavelength, $\mu_s'(\lambda)$ is the wavelength-specific value of the reduced scattering coefficient, $f_x$ is the spatial frequency of the structured light, $\eta$ is a predetermined constant, and each of $\zeta_i$, i=1, 2, 3, and 4, is a predetermined constant.

(A27) In the method denoted as (A26), the spectral wavelengths may be within spectral range of visible and near-infrared light and may be greater than 500 nanometers, the material may be biological tissue, and, in the step of fitting, the model may assume that $\mu_s'(\lambda) = a(\lambda/\lambda_0)^{-b}$, wherein a and b are constants and $\lambda_0$ is a reference wavelength.

(A28) In the method denoted as (A27), the step of fitting may include fitting the model to the intensities using fitting parameters: a, b, and $\gamma(\lambda)$ for each of the plurality of spectral wavelengths.

(A29) In any of the methods denoted as (A1) through (A28), the material may be biological tissue.

(A30) The method denoted as (A29) may further include deriving, from the backscatter likelihood, information about sub-cellular morphology of the biological tissue.

(B1) A structured-light imaging system for determining sub-diffuse scattering parameters of a material may include (a) a structured-light illuminator for illuminating the material with structured light of periodic spatial structure, (b) a camera for capturing images of remission of the structured light by the material, and (c) an analysis module for processing the images to quantitatively determine the sub-diffuse scattering parameters.

(B2) The structured-light imaging system denoted as (B1) may be configured for the optical axis of the camera being axis substantially orthogonal to surface of the material.

(B3) Either or both of the structured-light imaging systems denoted as (B1) and (B2) may further include a substantially optically clear, planar substrate for flattening surface of the material to reduce non-uniformity, in the images, caused by non-planar surface of the material.

(B4) In any of the structured-light imaging systems denoted as (B1) through (B3), the sub-diffuse scattering parameters may include reduced scattering coefficient and backscatter likelihood.

(B5) In any of the structured-light imaging systems denoted as (B1) through (B4), the structured-light imaging system may further include a control module configured to (a) control the structured-light illuminator to produce the periodic spatial structure at a plurality of spatial frequencies and, for each of the spatial frequencies, at a plurality of spatial phase shifts, and (b) control the camera to capture a plurality of frequency-specific image sets each associated with a respective one of the spatial frequencies and including an image at each of the spatial phase shifts.

(B6) In the structured-light imaging system denoted as (B5), the analysis module may include (1) a demodulator configured to process the plurality of frequency-specific image sets to produce a respective plurality of demodulated images substantially unaffected by the periodic spatial structure and indicating demodulated remission of the structured light at the respective plurality of spatial frequencies, (2) a model describing the demodulated remission as a function of (i) the reduced scattering coefficient, (ii) the backscatter likelihood, and (iii) spatial frequency of the period spatial structure, and (3) an optimizer configured to fit the model to the demodulated remission, indicated by the demodulated images, to determine the reduced scattering coefficient and the backscatter likelihood.

(B7) In the structured-light imaging system denoted as (B6), the structured-light illuminator may include a multichromatic light source for generating the structured light at a plurality of wavelengths.

(B8) In the structured-light imaging system denoted as (B7), the control module may include a wavelength selector unit configured to control the structured-light illuminator to produce the periodic spatial structure at each of the wavelengths and, for each of the wavelengths, produce the period spatial structure at the plurality of spatial frequencies and, for each of the spatial frequencies, at the plurality of spatial phase shifts.

(B9) In the structured-light imaging system denoted as (B8), the wavelength selector unit may further be configured to control the camera to capture a plurality of wavelength-specific image sets, wherein each wavelength-specific image set includes a plurality of frequency-specific image sets each associated with a respective one of the spatial frequencies and including an image at each of the spatial.

(B10) In the structured-light imaging system denoted as (B9), the model may describe the demodulated remission being wavelength dependent, and the optimizer may be configured to fit the model to the demodulated remission, indicated by all the demodulated images associated with all the wavelengths, to determine wavelength-specific values of the scattering coefficient and the backscatter likelihood for all the wavelengths.

(B11) In any of the structured-light imaging systems denoted as (B5) through (B10), the spatial frequencies may include (a) a lower spatial frequency sufficiently low that the remission associated therewith is sensitive to the reduced scattering coefficient, and (b) a higher spatial frequency sufficiently high that the remission associated therewith is sensitive to the backscatter likelihood.

(B12) In the structured-light imaging system denoted as (B11), the spatial frequencies may further include a spatial frequency of substantially zero to provide a measurement of absorption coefficient of the material.

(B13) In either or both of the structured-light imaging systems denoted as (B11) and (B12), the lower spatial frequency may correspond to interrogation depth, of the material, associated at least in part with diffuse scattering, and the higher spatial frequency may correspond to interrogation depth, of the material, associated at least in part with sub-diffuse scattering.

(B14) Any of the structured-light imaging systems denoted as (B1) through (B13) may implement the analysis module in a microprocessor.

(C1) A software product for analyzing images of remission of structured light by a material to determine sub-diffuse scattering parameters of the material (wherein the structured light has periodic spatial structure) may include machine-readable instructions encoded in non-transitory medium, wherein the machine-readable instructions include (a) demodulation instructions that, upon execution by a processor, process several image sets, respectively associated with several frequencies $f_x$ of the period spatial structure and, for each of the several frequencies, including a plurality of images associated with a respective plurality of spatial phase shifts of the period spatial structure, to produce several demodulated images substantially unaffected by the periodic spatial structure and indicating demodulated remission of the structured light at the several frequencies, respectively, (b) a model describing the demodulated remission as a function of (i) the reduced scattering coefficient $\mu'_s$, (ii) the backscatter likelihood $\gamma$, and (iii) spatial frequency $f_x$ of the period spatial structure, and (c) optimization instructions that, upon execution by a processor, fit the model to the demodulated remission, indicated by the demodulated images, to determine reduced scattering coefficient $\mu'_s$ and backscatter likelihood $\gamma$ for the material.

(C2) In the software product denoted as (C1), the backscatter likelihood may be defined as $\gamma=(1-g2)/(1-g1)$, wherein g1 and g2 are first and second Legendre moments, respectively, of scattering phase function of the material.

(C3) In either of both of the software products denoted as (C1) and (C2), the model may be $$R_d(\mu'_s, \gamma, f_x) = \eta\left(1 + (\zeta_4\gamma^{-2})(\mu'_s f_x^{-1})^{(-\zeta_3\gamma)}\right)\left[\frac{(\mu'_s f_x^{-1})^{(-\zeta_2\gamma)}}{\zeta_1\gamma^2 + (\mu'_s f_x^{-1})^{(-\zeta_2\gamma)}}\right],$$

wherein $R_d$ is the demodulated remission, $\eta$ is a predetermined constant, and each of $\zeta_i$, i=1, 2, 3, and 4, is a predetermined constant.

(C4) In any of the software products denoted as (C1) through (C3), the machine-readable instructions for step of fitting may include instructions for fitting the model to the demodulated remission using $\mu'_s$ and $\gamma$ as fitting parameters.

(C5) In any of the software products denoted as (C1) through (C4), the machine-readable instructions may further include multi-wavelength demodulation instructions that, upon execution by a processor, apply the demodulation instructions to a plurality of the several image sets, wherein the plurality of the several image sets are respectively associated with a plurality of spectral wavelengths of the structured light, to produce a plurality of the several demodulated images respectively associated with the plurality of spectral wavelengths.

(C6) In the software product denoted as (C5), the model may include a wavelength-sensitive model describing the demodulated remission as a function of (a) the reduced scattering coefficient $\mu'_s$, (b) the backscatter likelihood $\gamma$, and (c) spatial frequency $f_x$ of the period spatial structure, wherein $\mu'_s$ and $\gamma$ are wavelength dependent.

(C7) In the software product denoted as (C6), the optimization instructions may include multi-wavelength optimization instructions that, upon execution by a processor, fit the model to the plurality of the several demodulated images to determine the reduced scattering coefficient $\mu'_s$ and the backscatter likelihood $\gamma$ for each of the plurality of spectral wavelengths.

(C8) In the software product denoted as (C7), the wavelength-sensitive model may be $$R_d(\mu'_s(\lambda), \gamma(\lambda), f_x) = \eta\left(1 + (\zeta_4(\gamma(\lambda))^{-2})(\mu'_s(\lambda)f_x^{-1})^{(-\zeta_3(\gamma))}\right) \times \left[\frac{(\mu'_s(\lambda)f_x^{-1})^{(-\zeta_2\gamma(\lambda))}}{\zeta_1(\gamma(\lambda))^2 + (\mu'_s(\lambda)f_x^{-1})^{(-\zeta_2\gamma(\lambda))}}\right],$$

wherein $\lambda$ is spectral wavelength of the structured light and $\mu'_s(\lambda)$ is a predetermined function $\lambda$.

(C9) In any of the software products denoted as (C6) through (C8), the spectral wavelengths may be within spectral range of visible and near-infrared light and being greater than 500 nanometers, the material being biological tissue, and the wavelength-sensitive model may assume that $\mu'_s(\lambda)=a(\lambda/\lambda_0)^{-b}$, wherein a and b are constants and $\lambda_0$ is a reference wavelength.

(C10) In the software product denoted as (C9), the optimization instructions may include instructions that, upon execution by the processor, fit the model to the plurality of the several demodulated images using fitting parameters: a, b, and $\gamma(\lambda)$ for each of the plurality of spectral wavelengths.

Changes may be made in the above systems and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present system and method, which, as a matter of language, might be said to fall therebetween.

What is claimed is:

1. A method for determining sub-diffuse scattering parameters of a material, the method operable on a structured light imaging machine, comprising:
   illuminating the material with structured light of a plurality of phase shifts, the structured light provided by a structured light illuminator adapted to provide structured light at a plurality of spatial frequencies;
   imaging remission by the material of the structured light with a digital camera; and
   determining, in an analysis module, from images captured in the step of imaging, sub-diffuse scattering parameters of the material;
   wherein the step of illuminating comprises, at a spectral wavelength of the structured light, temporally varying periodic structure of the structured light to produce each of a plurality of spatial frequencies and, for each of the plurality of spatial frequencies, a plurality of spatial phase shifts;
   the step of imaging comprising capturing a plurality of images including an image of the remission for each of the plurality of spatial phase shifts associated with each of the plurality of spatial frequencies; and
   the step of determining comprising processing the plurality of images to deduce wavelength-specific values of the sub-diffuse scattering parameters;
   the step of determining comprises:
      generating demodulated images respectively associated with the plurality of spatial frequencies, each of the demodulated images being generated from the plurality of images captured for a respective one of the plurality of spatial frequencies; and
      fitting a wavelength dependent model for demodulated remission to the plurality of images, the wavelength dependent model sensitive to (a) the wavelength-specific values of the sub-diffuse scattering parameters and (b) spatial frequency of the periodic structure, to intensities in the demodulated images, to ascertain the wavelength-specific values of the sub-diffuse scattering parameters.

2. The method of claim 1 wherein the sub-diffuse scattering parameters include reduced scattering coefficient and backscatter likelihood.

3. The method of claim 1, the step of fitting being performed independently for each of at least some of all spatial locations represented by the demodulated images, to produce a spatial map of the wavelength-specific values of the sub-diffuse scattering parameters.

4. The method of claim 3 further comprising using the spatial map of the wavelength-specific values of the sub-diffuse scattering parameters to assess tissue.

5. The method of claim 4 wherein the assessing tissue comprises assessing tissue incorporating a wound.

6. The method of claim 4 wherein the assessing tissue comprises diagnosing cancer.

7. The method of claim 4 wherein the assessing tissue comprises assessing brain tissue.

8. The method of claim 1 wherein the spatial modulator comprises a light source providing light to a spatial modulator selected from the group consisting of a liquid crystal display and a digital multimirror device.

9. A method for determining sub-diffuse scattering parameters of a material, the method operable on a structured light imaging machine, comprising:
   illuminating the material with structured light of a plurality of phase shifts, the structured light provided by a structured light illuminator adapted to provide structured light at a plurality of spatial frequencies;
   imaging remission by the material of the structured light with a digital camera; and
   determining, in an analysis module, from images captured in the step of imaging, sub-diffuse scattering parameters of the material;
   wherein the step of illuminating comprises, at a spectral wavelength of the structured light, temporally varying periodic structure of the structured light to produce each of a plurality of spatial frequencies and, for each of the plurality of spatial frequencies, a plurality of spatial phase shifts;
      the step of imaging comprising capturing a plurality of images including an image of the remission for each of the plurality of spatial phase shifts associated with each of the plurality of spatial frequencies; and
      the step of determining comprising processing the plurality of images to deduce wavelength-specific values of the sub-diffuse scattering parameters;
   the step of determining comprises:
      generating demodulated images respectively associated with the plurality of spatial frequencies, each of the demodulated images being generated from the plurality of images captured for a respective one of the plurality of spatial frequencies; and
      fitting a wavelength dependent model for demodulated remission to the plurality of images, the wavelength dependent model sensitive to (a) the wavelength-specific values of the sub-diffuse scattering parameters and (b) spatial frequency of the periodic structure, to intensities in the demodulated images, to ascertain the wavelength-specific values of the sub-diffuse scattering parameters;
   the step of fitting being performed independently for each of at least some of all spatial locations represented by the demodulated images, to produce a spatial map of the wavelength-specific values of the sub-diffuse scattering parameters;
      the step of fitting comprising ascertaining a wavelength-specific value of the backscatter likelihood as $\gamma=(1-g2)/(1-g1)$, wherein g1 and g2 are first and second Legendre moments, respectively, of a scattering phase function of the material; and
      in the step of fitting, the wavelength dependent model specifying remission as a function of $\gamma$ and product between (a) a wavelength-specific value of the reduced scattering coefficient and (b) spatial frequency of the structured light.

10. The method of claim 9 wherein the spatial modulator comprises a light source providing light to a spatial modulator selected from the group consisting of a liquid crystal display and a digital multimirror device.

11. The method of claim 9 wherein the sub-diffuse scattering parameters include reduced scattering coefficient and backscatter likelihood.

12. The method of claim 9 further comprising using the spatial map of the wavelength-specific values of the sub-diffuse scattering parameters to assess tissue.

13. The method of claim 9 wherein the assessing tissue comprises assessing tissue incorporating a wound.

14. The method of claim 9 wherein the assessing tissue comprises diagnosing cancer.

15. The method of claim 9 wherein the assessing tissue comprises assessing brain tissue.

* * * * *